(12) United States Patent
Jeyachandran

(10) Patent No.: US 12,133,946 B2
(45) Date of Patent: Nov. 5, 2024

(54) DURABLE, MULTI-USE PERITONEAL DIALYSIS CYCLER USING DISINFECTION

(71) Applicants: BAXTER INTERNATIONAL INC., Deerfield, IL (US); BAXTER HEALTHCARE SA, Glattpark (CH)

(72) Inventor: Ramkumar Jeyachandran, Bangalore (IN)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 0 days.

(21) Appl. No.: 18/269,850

(22) PCT Filed: Dec. 8, 2021

(86) PCT No.: PCT/US2021/062363
§ 371 (c)(1),
(2) Date: Jun. 27, 2023

(87) PCT Pub. No.: WO2022/146638
PCT Pub. Date: Jul. 7, 2022

(65) Prior Publication Data
US 2024/0269362 A1    Aug. 15, 2024

(30) Foreign Application Priority Data
Dec. 29, 2020 (IN) .............................. 202041056858

(51) Int. Cl.
*A61M 1/28* (2006.01)
*A61M 1/16* (2006.01)

(52) U.S. Cl.
CPC ............ *A61M 1/282* (2014.02); *A61M 1/168* (2013.01)

(58) Field of Classification Search
CPC ...................... A61M 1/1688; A61M 1/28–288
See application file for complete search history.

(56) References Cited

U.S. PATENT DOCUMENTS 5,256,371 A * 10/1993 Pippert ................. A61M 1/169
                                                  210/636
5,304,349 A *  4/1994 Polaschegg ........... A61M 1/169
                                                  422/534
(Continued)

OTHER PUBLICATIONS

International Preliminary Report on Patentability for PCT/US2021/062363 dated Feb. 23, 2023—11 pages.
(Continued)

*Primary Examiner* — Kami A Bosworth
(74) *Attorney, Agent, or Firm* — K&L Gates LLP

(57) ABSTRACT

A peritoneal dialysis system includes: a dialysis fluid pump including a pump actuator and a dialysis fluid contacting portion actuated by the pump actuator; a fresh dialysis fluid valve located upstream of the pump and including a fresh valve actuator and a dialysis fluid contacting portion actuated by the fresh valve actuator; a patient line valve located downstream of the pump and including a patient line valve actuator and a dialysis fluid contacting portion actuated by the patient line valve actuator; a drain valve positioned and arranged to receive used dialysis fluid from the patient and including a drain valve actuator and a dialysis fluid contacting portion; a patient line extending from the drain valve; and a fluid loop including dialysis fluid contacting portions of the pump, the fresh dialysis fluid valve, the patient line valve and the drain valve, and wherein the patient line extends from the fluid loop.

15 Claims, 15 Drawing Sheets

(56) References Cited

U.S. PATENT DOCUMENTS

| | | | |
|---|---|---|---|
| 2009/0012450 A1 | 1/2009 | Shah et al. | |
| 2012/0273354 A1* | 11/2012 | Orhan | A61M 1/14 204/627 |
| 2016/0166753 A1* | 6/2016 | Meyer | A61M 1/1621 422/38 |
| 2017/0281845 A1* | 10/2017 | Manda | A61L 2/0047 |
| 2019/0125954 A1 | 5/2019 | Mathiot | |
| 2020/0129927 A1* | 4/2020 | Sendelius | B01D 61/58 |
| 2023/0014172 A1* | 1/2023 | Tsoory | A61M 1/1696 |

OTHER PUBLICATIONS

International Search Report for PCT/US2021/062363 dated Jul. 12, 2022—6 pages.

Written Opinion for PCT/US2021/062363 dated Jul. 12, 2022—13 pages.

\* cited by examiner

DURABLE, MULTI-USE PERITONEAL DIALYSIS CYCLER USING DISINFECTION

PRIORITY CLAIM

The present application is a national phase entry of PCT Patent Application No. PCT/US2021/062363, filed on Dec. 8, 2021, which claims priority to and the benefit of Indian Patent Application No. 202041056858, filed on Dec. 29, 2020, the entirety of which is herein incorporated by reference.

BACKGROUND

The present disclosure relates generally to medical fluid treatments and in particular to dialysis fluid treatments.

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD, HF, and HDF treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products and render less interdialytic fluid overload than a patient receiving less frequent but perhaps longer treatments. A patient receiving more frequent treatments does not experience as much of a down cycle (swings in fluids and toxins) as does an in-center patient, who has built-up two or three days' worth of toxins prior to a treatment. In certain areas, the closest dialysis center can be many miles from the patient's home, causing door-to-door treatment time to consume a large portion of the day. Treatments in centers close to the patient's home may also consume a large portion of the patient's day. HHD can take place overnight or during the day while the patient relaxes, works or is otherwise productive.

Another type of kidney failure therapy is peritoneal dialysis ("PD"), which infuses a dialysis solution, also called dialysis fluid, into a patient's peritoneal chamber via a catheter. The dialysis fluid is in contact with the peritoneal membrane in the patient's peritoneal chamber. Waste, toxins and excess water pass from the patient's bloodstream, through the capillaries in the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used or spent dialysis fluid to drain from the peritoneal chamber. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal chamber, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal chamber. APD machines also allow for the dialysis fluid to dwell within the chamber and for the transfer of waste, toxins and excess water to take place. The source may include multiple liters of dialysis fluid including several solution bags.

APD machines pump used or spent dialysate from the patient's peritoneal cavity, though the catheter, and to the drain. As with the manual process, several drain, fill and dwell cycles occur during dialysis. A "last fill" may occur at the end of the APD treatment. The last fill fluid may remain in the peritoneal chamber of the patient until the start of the next treatment, or may be manually emptied at some point during the day.

In any of the above modalities using an automated machine, the automated machine operates typically with a disposable set, which is discarded after a single use. Depending on the complexity of the disposable set, the cost of using one set per day may become significant. Also, daily disposables require space for storage, which can become a nuisance for home owners and businesses. Moreover, daily disposable replacement requires daily setup time and effort by the patient or caregiver at home or at a clinic.

For each of the above reasons, it is desirable to provide an APD machine that reduces disposable waste.

SUMMARY

Known automated peritoneal dialysis ("PD") systems typically include a machine or cycler that accepts and actuates a pumping cassette having a hard part and a soft part that is deformable for performing pumping and valving operations. The hard part is attached to tubes that extend to various bags. The disposable cassette and associated tubes and bags can be cumbersome for a patient at home to load for treatment. The overall amount of disposable items may also lead to multiple setup procedures requiring input from the patient, which can expose room for error.

The APD system and associated methodology of the present disclosure, on the other hand, converts much of the fluid carrying portions of its PD system into reusable components, which are disinfected after treatment. Fluid handling and sensing components and fluid lines within the machine or cycler are reused. Disposable items remaining may include solution bags and associated lines, a patient line, a drain line leading to a drain bag or house drain, a disinfection container or bag and associated line, and possibly an ultrafiltration or sample container. At least some of those lines may be disinfected and reused alternatively.

A first primary embodiment of the system and method of the present disclosure, includes two pumps, for example peristaltic pumps, wherein one pump is dedicated to pumping fresh dialysis fluid to the patient, while the second pump is dedicated to removing used dialysis fluid from the patient. The lines leading to and from the pumps, and the pumping tubes operating with the pumps, are reused and disinfected after treatment. The disposable items that the patient connects for treatment may include first and second dialysis fluid containers or bags, a drain line leading to a house drain or drain bag, and a patient line. In an embodiment, those lines connect in a sterilized fashion to the PD machine or cycler.

The first primary embodiment also includes multiple valves, such as three-way and two-way valves, which may be electrically actuated valves. The valves are positioned to allow fresh dialysis fluid to be drawn from a desired source, to allow dialysis fluid to be pushed to or removed from the patient, and to allow the PD machine or cycler to operate in a treatment mode or a disinfection mode.

The first primary embodiment further includes flow sensors, such as a fresh dialysis fluid flow sensor and a used dialysis fluid flow sensor, which are used to determine solution volumes, such as a volume of fresh fluid delivered to the patient, used fluid removed from the patient and a difference between the two, which is patient ultrafiltration removal. An inline heater may also be positioned adjacent a temperature sensor, which are used for both dialysis fluid heating and disinfection. A pressure sensor and conductivity sensor may be placed near the patient to ensure proper patient filling and draining. The cycler of the first primary embodiment also includes flexible lines or paths, which are used after treatment is completed. [As will be illustrated herein, many of the components of the first primary embodiment, such as the heater and temperature sensor, pressure and conductivity sensors, and the flexible lines or paths used after treatment, are also provided with the other primary embodiments discussed herein.

All pumps, valves, heater and sensors are under control of or output to a control unit, which includes one or more processor and one or more memory. The control unit of the first primary embodiment may be programmed to control the fresh dialysis fluid pump to push fresh dialysis fluid through the heater and past the temperature sensor that verifies proper treatment temperature (e.g., 37° C.). The fresh dialysis fluid is also pumped through the fresh dialysis fluid flow sensor, which indicates a flowrate that is integrated over time to determine and control a total amount of fresh, heated dialysis fluid delivered to the patient for a subsequent dwell. The fresh peristaltic pump provides a smooth delivery to the patient. The downstream pressure sensor may be a back-pressure sensor that monitors the patient's intraperitoneal pressure to prevent overfilling and/or overpressurizing the patient. The downstream conductivity sensor may be used to confirm that the prescribed dialysis fluid having the proper mix is being delivered to the patient.

The first primary embodiment also includes an effluent pump, e.g., a peristaltic pump that is smooth and generally continuous, which pulls effluent from the patient. Here, the pressure sensor monitors a negative pressure that the effluent pump applies to the patient to avoid patient discomfort during drain. Used dialysis fluid flows past the conductivity sensor, the output of which can be used to look for certain markers in the effluent or used dialysis fluid (e.g., for peritonitis). The downstream flow sensor indicates effluent flowrate, which is integrated over time to determine a total amount of used dialysis fluid or effluent removed from the patient after dwell. The total amount of effluent removed less the total amount of fresh dialysis fluid delivered to the patient indicates an amount of ultrafiltration ("UF") removed from the patient over the corresponding dwell period.

During a patient fill phase, the control unit causes one or both of the two fresh dialysis fluid three-way valves to open depending upon which dialysis fluid container is being used. The control unit further causes the patient line valve to be open and the drain line valve to be closed. After the fill phase in which a prescribed amount of fresh dialysis fluid is delivered by the fresh dialysis fluid pump to the patient as measured by the fresh dialysis fluid flow sensor, the control unit proceeds to a dwell phase in which all valves are closed in one embodiment. After the dwell phase, the control unit proceeds to a patient drain phase, wherein the fresh dialysis fluid valves are closed, while the patient line and drain line valves are open. The control unit causes the used dialysis fluid pump to remove a prescribed or minimum amount of used dialysis fluid from the patient (or until the patient is empty) as measured by the used dialysis fluid flow sensor.

After treatment, the system and method of the first primary embodiment of the present disclosure is disinfected. Here, in one embodiment, the dialysis fluid containers are disconnected from the cycler. The patient line is disconnected from the patient and connected instead to the drain line, which may have been disconnected from the drain. Or, one of the patient or drain lines is removed and the other is connected to a connection point of the removed line, completing a disinfection circuit.

The reusable cycler circuit may be heat and/or chemical disinfected. In one embodiment, one of the fresh dialysis fluid valves is connected to a disinfection, e.g., citric acid, container, while the other fresh dialysis fluid valves is connected to a source of purified water. The control unit causes the fresh dialysis fluid pumps to push disinfectant solution from the disinfection source passed the heater, which heats the solution to a sterilizing temperature of, e.g., 90° C. The control unit opens the patient valve to allow hot, e.g., citric acid solution to be recirculated to the drain. The patient valve is then closed, while the fresh dialysis fluid and drain valves are opened to allow the control unit to cause the effluent pump and the fresh dialysis fluid pump to circulate hot disinfectant through the closed loop for a predetermined disinfection time at a predetermined temperature. At the end of disinfection, the drain valve is opened to drain. The control unit switches the valves and operates the pumps so that water from the water source is rinsed through the system to purge disinfectant residuals to drain. The system is then ready for another treatment.

In an alternative implementation of the first primary embodiment, a UF or sample bag is added to one of the ports of the three-way drain valve. A fifth valve (e.g., three-way) is added for disinfection. Fill, dwell and drain phases are handled in a manner similar to the first primary embodiment not having the UF or sample bag using fresh and used dialysis fluid pumps. Disinfection again involves connecting the patient line valve fluidly to the drain line valve in some manner.

In a second primary embodiment, the system provides a single pump having otherwise the same components as the first primary embodiment including the three three-way valves (two fresh fluid valves and a drain valve) and the two-way patient line valve, flow sensors including a fresh dialysis fluid flow sensor and a used dialysis fluid flow sensor, an inline heater positioned adjacent a temperature sensor, a pressure sensor and conductivity sensor placed along the patient to ensure proper patient filling and draining. Each of the above components is under control of or outputs to a control unit.

In the single pump version, the effluent or drain valve is located between the pump and the patient line valve, so that the control unit causes the pump to pump fresh dialysis fluid through one or both of the upstream fresh dialysis fluid valves, the downstream valve, and the two-way patient valve to the patient. Effluent is pumped by the single pump from the patient, through both upstream dialysis fluid valves and the drain or effluent valve, to drain. During disinfection of the single pump embodiment, the patient line valve is connected fluidly to the drain line valve, the dialysis fluid containers are removed and disinfection and water sources are connected fluidly to the fluid circuit, the same as with the dual pump first primary embodiment.

In an alternative implementation of the second primary embodiment, a UF or sample bag is added to one of the ports of an additional fifth valve (e.g., three-way). Fill, dwell and drain phases are handled in a manner similar to the second primary embodiment not having the UF or sample bag using a single dialysis fluid pump. Disinfection involves connecting the patient line valve, drain line and UF line fluidly to a drain container, which is also connected fluidly to an additional fifth valve.

In light of the disclosure set forth herein, and without limiting the disclosure in any way, in a first aspect of the present disclosure, which may be combined with any other aspect described herein, a peritoneal dialysis ("PD") system includes: a dialysis fluid pump including a pump actuator and a dialysis fluid contacting portion actuated by the pump actuator; a fresh dialysis fluid valve located upstream of the dialysis fluid pump, the fresh dialysis fluid valve including a fresh valve actuator and a dialysis fluid contacting portion actuated by the fresh valve actuator; a patient line valve located downstream of the dialysis fluid pump, the patient line valve including a patient line valve actuator and a dialysis fluid contacting portion actuated by the patient line valve actuator; a drain valve positioned and arranged to receive used dialysis fluid from the patient, the drain valve including a drain valve actuator and a dialysis fluid contacting portion; and a control unit configured to (i) cause the pump actuator, fresh valve actuator, patient line valve actuator and drain valve actuator to actuate or not actuate their respective dialysis fluid contacting portion according to a programmed fill sequence to perform a PD fill phase, (ii) cause the pump actuator, fresh valve actuator, patient line valve actuator and drain valve actuator to actuate or not actuate their respective dialysis fluid contacting portion according to a programmed drain sequence to perform a PD drain phase, and (iii) after (i) and (ii), or after (i) and (ii) are repeated at least one time, cause the pump actuator, fresh valve actuator, patient line valve actuator and drain valve actuator to actuate or not actuate their respective dialysis fluid contacting portion according to a programmed disinfection sequence to disinfect the respective dialysis fluid contacting portions of each of the pump actuator, fresh valve actuator, patient line valve actuator and drain valve actuator.

In a second aspect of the present disclosure, which may be combined with any other aspect described herein, the disinfection sequence is further configured to disinfect at least one of (a) a first fluid line leading from a dialysis fluid source to the dialysis fluid contacting portion of the fresh valve actuator, (b) a second fluid line leading from the dialysis fluid contacting portion of the fresh valve actuator to the dialysis fluid contacting portion of the pump actuator, (c) a third fluid line leading from the fluid contacting portion of the pump actuator, (d) a fourth fluid line patient line leading to the fluid contacting portion of the patient line valve actuator, (e) a fifth fluid line leading from the fluid contacting portion of the patient line valve actuator, (f) a sixth fluid line patient line leading to the fluid contacting portion of the drain valve actuator, or (g) a seventh fluid line patient line leading from the fluid contacting portion of the drain valve actuator.

In a third aspect of the present disclosure, which may be combined with any other aspect described herein, at least one of the first to the seventh fluid lines of the second aspect is made of metal or a biocompatible and heat-disinfectable flexible tube.

In a fourth aspect of the present disclosure, which may be combined with any other aspect described herein, the fluid contacting portion of at least one of the fresh valve actuator, the patient line valve actuator or the drain valve actuator includes a tube or membrane.

In a fifth aspect of the present disclosure, which may be combined with any other aspect described herein, the fluid contacting portion of at least one of the fresh valve actuator, the patient line valve actuator or the drain valve actuator includes an internal cavity of the respective actuator.

In a sixth aspect of the present disclosure, which may be combined with any other aspect described herein, the fluid contacting portion of the pump actuator incudes a tube or membrane.

In a seventh aspect of the present disclosure, which may be combined with any other aspect described herein, the fluid contacting portion of the pump actuator incudes an internal cavity of the pump actuator.

In an eighth aspect of the present disclosure, which may be combined with any other aspect described herein, the fluid contacting portion of the patient line valve actuator is placed in fluid communication with the fluid contacting portion of the drain line valve actuator for operation of the programmed disinfection sequence.

In a ninth aspect of the present disclosure, which may be combined with any other aspect described herein, the fluid contacting portion of the patient line valve actuator is placed in fluid communication with a drain container connected fluidly with the fluid contacting portion of the drain line valve actuator for operation of the programmed disinfection sequence.

In a tenth aspect of the present disclosure, which may be combined with any other aspect described herein, a dialysis fluid source placed in fluid communication with the dialysis fluid contacting portion of the fresh valve actuator for the PD fill phase in (i) is replaced by a source of disinfectant for the programmed disinfection sequence in (iii).

In an eleventh aspect of the present disclosure, which may be combined with any other aspect described herein, the fresh dialysis fluid valve is a first fresh dialysis fluid valve, and which includes a second fresh dialysis fluid valve located upstream of the dialysis fluid pump, the second fresh dialysis fluid valve including a second fresh valve actuator and a second dialysis fluid contacting portion actuated by the second fresh valve actuator, wherein first and second dialysis fluid sources placed in fluid communication with the first and second dialysis fluid contacting portions of the respective first and second fresh valve actuators for the PD fill phase in (i) are replaced by a source of disinfectant and a source of purified water for the programmed disinfection sequence in (iii).

In a twelfth aspect of the present disclosure, which may be combined with any other aspect described herein, the control unit is configured to use the dialysis fluid pump to pump fresh dialysis fluid during the fill phase in (i) and to pump used dialysis fluid during the drain phase in (ii).

In a thirteenth aspect of the present disclosure, which may be combined with any other aspect described herein, the dialysis fluid pump is a fresh dialysis fluid pump including a fresh dialysis fluid pump actuator for pumping fresh dialysis fluid during the fill phase in (i), and which includes a used dialysis fluid pump including a used dialysis fluid pump actuator for pumping used dialysis fluid during the drain phase in (ii), and wherein the control unit is configured to cause the fresh dialysis fluid pump actuator, used dialysis fluid pump actuator, fresh valve actuator, patient line valve actuator and drain valve actuator to actuate or not actuate their respective dialysis fluid contacting portion according to the programmed disinfection sequence.

In a fourteenth aspect of the present disclosure, which may be combined with any other aspect described herein, the fresh dialysis fluid pump actuator and the used dialysis fluid pump actuator are actuated during the programmed disinfection sequence, and wherein at least a portion of each of the fresh valve actuator, patient line valve actuator and drain valve actuator is fluidically open during the programmed disinfection sequence.

In a fifteenth aspect of the present disclosure, which may be combined with any other aspect described herein, the dialysis fluid pump actuator is actuated during the programmed disinfection sequence, and wherein at least a portion of each of the fresh valve actuator, patient line valve actuator and drain valve actuator is fluidically open during the programmed disinfection sequence.

In a sixteenth aspect of the present disclosure, which may be combined with any other aspect described herein, a peritoneal dialysis ("PD") system includes: a dialysis fluid pump including a pump actuator and a dialysis fluid contacting portion actuated by the pump actuator; a fresh dialysis fluid valve located upstream of the dialysis fluid pump, the fresh dialysis fluid valve including a fresh valve actuator and a dialysis fluid contacting portion actuated by the fresh valve actuator; a patient line valve located downstream of the dialysis fluid pump, the patient line valve including a patient line valve actuator and a dialysis fluid contacting portion actuated by the patient line valve actuator; a drain valve positioned and arranged to receive used dialysis fluid from the patient, the drain valve including a drain valve actuator and a dialysis fluid contacting portion; a patient line extending from the drain valve; and a fluid loop including dialysis fluid contacting portions of the dialysis fluid pump, the fresh dialysis fluid valve, the patient line valve and the drain valve, and wherein the patient line extends from the fluid loop.

In a seventeenth aspect of the present disclosure, which may be combined with any other aspect described herein, the system includes a control unit configured to perform a disinfection sequence in which a disinfection fluid is circulated through the fluid loop.

In an eighteenth aspect of the present disclosure, which may be combined with any other aspect described herein, the disinfection fluid is at least one of a chemical disinfectant or a heated fluid.

In an nineteenth aspect of the present disclosure, which may be combined with any other aspect described herein, the dialysis fluid contacting portions of the patient line valve and the drain valve are linked via a fluid connection during the disinfection sequence, wherein the disinfection fluid is further circulated through the fluid connection.

In a twentieth aspect of the present disclosure, which may be combined with any other aspect described herein, a dialysis fluid pump is a first dialysis fluid pump, and which includes a second pump actuator and a second dialysis fluid contacting portion actuated by the second pump actuator, and wherein the second dialysis fluid contacting portion is part of the fluid loop.

In a twenty-first aspect, any of the features, functionality and alternatives described in connection with any one or more of FIGS. 1 to 15 may be combined with any of the features, functionality and alternatives described in connection with any other of FIGS. 1 to 15.

It is accordingly an advantage of the present disclosure to provide a relatively volumetrically accurate automated peritoneal dialysis ("APD") cycler.

It is another advantage of the present disclosure to provide an APD cycler that achieves relatively precise pressure control.

It is yet another advantage of the present disclosure to provide an APD cycler that is capable of inline volume measurement of ultrafiltration ("UF") for each treatment and for automated sharing of UF results with clinics and doctors.

It is still another advantage of the present disclosure to provide an APD cycler that is capable of inline measurement of toxin removal during treatment and for automated sharing of such results with clinics and doctors.

Further still, it is an advantage of the present disclosure to provide an APD cycler that uses an inline heater that does not require an inline heating disposable, reducing treatment time and disposable cost.

It is a further advantage of the present disclosure to provide a relatively quiet APD cycler.

It is yet a further advantage of the present disclosure to provide a relatively simple and low cost APD cycler.

It is yet another advantage of the present disclosure to provide a relatively simple disposable set.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

Figure 1:
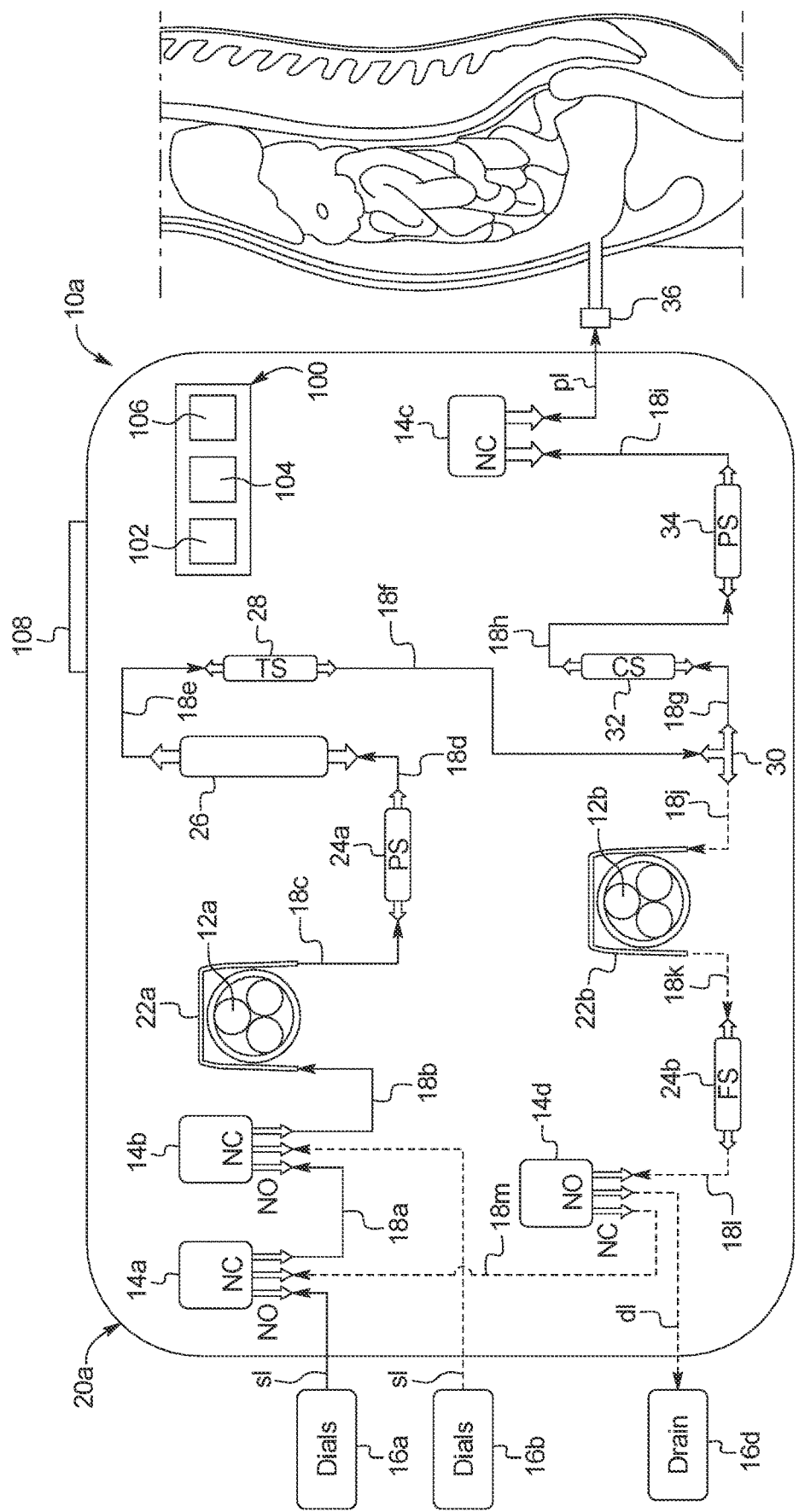
FIG. 1 is a flow schematic view of a first automated peritoneal dialysis ("APD") cycler embodiment of the present disclosure having fresh and effluent pumps, and which is configured for disinfection post treatment.

Referring now to the drawings and in particular to FIG. 1, a first primary embodiment of an automated peritoneal dialysis ("APD") system $10a$ and associated methodology of the present disclosure includes an APD machine or cycler $20a$, which is generally defined by the rectangular box in FIG. 1. In the illustrated embodiment, APD machine or cycler $20a$ includes fresh dialysis fluid pump $12a$ and used dialysis fluid pump $12b$. Pumps $12a$ and $12b$ are illustrated as peristaltic pumps, however, pumps $12a$ and $12b$ may be any type of fluid pump, for example a gear pump or a membrane pump, and may be of the same or different type. Due to the reusable nature of system $10a$, pumps $12a$ and $12b$ are not limited to types that operate with a disposable item, such as a tube or a flexible chamber. Pumps $12a$ and $12b$ instead may include or define internal, e.g., metallic or partially metallic, cavities that receive and contact a fluid to be pumped, such as fresh or used dialysis fluid. On the other hand, pumps $12a$ and $12b$ may be peristaltic or membrane pumps that operate with a tube, flexible chamber, or other flexible fluid contacting portion that would in other circumstances be disposable, but which here are disinfected after treatment or prior to a subsequent treatment.

Cycler $20a$ of system $10a$ includes a first fresh dialysis fluid valve $14a$ and a second fresh dialysis fluid valve $14b$ located upstream of fresh dialysis fluid pump $12a$. First fresh dialysis fluid valve $14a$ is communicated fluidly with a first source of fresh dialysis fluid $16a$ via a first solution line sl, while fresh dialysis fluid valve $14b$ is communicated fluidly with a second source of fresh dialysis fluid $16b$ via a second solution line sl. Dialysis fluid sources $16a$ and $16b$ may hold the same or different type of fresh dialysis fluid. Dialysis fluid sources $16a$ and $16b$ are premade containers or bags of fresh dialysis fluid in the illustrated embodiment, and solution lines sl may be provided and discarded with sources $16a$ and $16b$. In an alternative embodiment, either one or both sources $16a$ or $16b$ is an online peritoneal dialysis fluid source. Additionally, while two sources $16a$ and $16b$ and two valves $14a$ and $14b$ are illustrated, system $10a$ alternatively includes only one source and associated valve, or three or more sources and associated valves.

In the illustrated embodiment, valves $14a$ and $14b$ are electrically actuated three-way valves, with one port normally open ("NO"), that is, open while no energy is applied, and with another port normally closed ("NC"), that is, closed while no energy is applied. When energy is applied to valves $14a$ and $14b$, the ports switch states such that the NO port closes (restricts flow) and the NC port opens (allows flow). The third port of each valve $14a$ and $14b$ is always open and does not switch states. In the illustrated embodiment of FIG. 1, fresh dialysis fluid supply $16a$ is fluidly communicated via a first supply bag line to NO port of valve $14a$, while the third port of valve $14a$ is fluidly communicated via a reusable line $18a$ with the NO port of valve $14a$. Fresh dialysis fluid supply $16b$ is fluidly communicated via a second supply bag line to NC port of valve $14b$. Thus when treatment begins, no energy is needed at either valve $14a$ or $14b$ to allow flow from first fresh dialysis fluid supply $16a$. Here, fresh dialysis fluid pump $12a$ occludes flow until it is actuated, preventing free flow from fluid supply $16a$. After first fresh dialysis fluid supply $16a$ is consumed and it is time for flow from second fresh dialysis fluid supply $16b$, at least valve $14b$ and perhaps both valves $14a$ and $14b$ are energized to close NO port and open NC port of valve $14b$ to enable pump $12a$ to pump fresh dialysis fluid from second fresh dialysis fluid supply $16b$ through valve $14b$.

Due to the reuse of system $10$, any of the valves described herein, including valves $14a$ and $14b$, may include internal fluid contacting portions that are metallic or otherwise of a nature that would be cost prohibitive to discard after each treatment. In alternative embodiments, any of the valves described herein may operate with tubing (e.g., pinch valves) or flexible membranes (e.g., electric or pneumatic volcano valves), which are disinfected after treatment and reused. In still further alternative embodiments, any of the three-way valves described herein, including valves 14a and 14b, may be replaced via multiple two-way valves.

In FIG. 1, valve 14b is fluidly communicated with reusable fresh dialysis fluid pump line 22a of fresh dialysis fluid pump 12a via reusable line 18b. A reusable line 18c extends from reusable pump line 22a to a fresh dialysis fluid flow sensor 24a, e.g., an inline flow sensor. A reusable line 18d extends from fresh dialysis fluid flow sensor 24 to a dialysis fluid heater 26, e.g., an inline dialysis fluid heater. A reusable line 18e extends from dialysis fluid heater 26 to a dialysis fluid temperature sensor 28, e.g., an inline temperature sensor. A reusable line 18f extends from temperature sensor 28 to one port of a reusable T or Y connector 30. T or Y connector 30 separates a fluid loop (e.g., for disinfection) located to the left of the connector from a series of patient fluid delivery devices to the right of connector 30.

A reusable line 18g leads from connector 30 (to the right) to a conductivity sensor 32, e.g., an inline conductivity sensor. A reusable line 18h leads from conductivity sensor 32 to a pressure sensor 34, e.g., an inline pressure sensor. A reusable line 18i leads from pressure sensor 34 to a two-way normally closed valve 14c, which may be electrically actuated. Valve 14c may have any of the alternative structure and functionality discussed above for valves 14a and 14b. In an embodiment, a patient line pl leads from two-way normally closed valve 14c to a patient's transfer set 36, which extends to an indwelling catheter located within the patient's peritoneal cavity. Patient line pl may be disposable, e.g., after each treatment using system 10a, or reusable as with lines 18a to 18i.

A reusable line 18j leads from connector 30 (to the left) to reusable used dialysis fluid pump line 22b of used dialysis fluid pump 12b. Reusable line 18k leads from used dialysis fluid pump line 22b to a used dialysis fluid flow sensor 24b, e.g., an inline flow sensor. Reusable line 18l leads from used dialysis fluid flow sensor 24b to a three-way drain valve 14d, which may have one port normally open ("NO"), that is, open while no energy is applied, and another port normally closed ("NC"), that is, closed while no energy is applied. Any of the alternative embodiments discussed above for valves 14a and 14b are likewise applicable to drain valve 14d.

In the illustrated embodiment, reusable disinfection line 18l extends from a NC port of drain valve 14d to a NC port of fresh dialysis fluid valve 14a. NO port of drain valve 14d is connected to a drain container 16d via a drain line dl. Drain line dl may be reusable or disposable. Any of the reusable lines described herein, including reusable lines 18a to 18m, may be metal or plastic, e.g., of a stiffer and more durable plastic than typically used with disposable systems. The plastic is in one embodiment biocompatible, heat-disinfectable and flexible. Pump lines 22a and 22b, patient line pl and drain line dl and disinfection line 18m are likely flexible, e.g., plastic lines. Pump lines 22a and 22b, e.g., peristaltic pump lines, may be different or larger in diameter than the other lines and selected to have a desirable shore hardness for pumping. They may nevertheless be reused according to the disinfection routines discussed herein and likewise be biocompatible, heat-disinfectable and flexible.

Specifications and alternatives for pumps 12a and 12b and valves 14a to 14d are provided above. Flow sensors 24a and 24b as mentioned above may, but do not have to be, inline and invasive flow sensors. Invasive flow sensors or meters 24a and 24b may include rotary vane, vortex shedding, optical, magnetic and mass flow sensors for example. Non-invasive flow sensors may also be provided and include heat pulse, time of flight and optical flow sensors, for example.

The outputs from flow sensors or meters 24a and 24b are used as feedback to control pumps 12a and 12b to pump at a desired or specified flowrate, allowing the power delivered to the pumps to be varied as needed. The outputs from flow sensors or meters 24a and 24b are also integrated over time to yield (i) how much fresh dialysis fluid is delivered to the patient, (ii) how much used dialysis fluid is removed from the patient, and (iii) a difference between (ii) versus (i) to know how much ultrafiltration ("UF") or excess water has been removed from the patient.

Inline heater 26 heats fresh dialysis fluid from its starting temperature to body fluid temperature, e.g., 37° C., for comfortable delivery to the patient. Inline heater 26 may include a flow through and/or circulation heater. The output from temperature sensor 28 located downstream from dialysis fluid heater 26 is used as feedback to control the amount of heating power supplied to heater 26. The feedback allows the target temperature to be reached without significant overshoot. If needed for this or any embodiment discussed herein, an upstream temperature sensor (not illustrated) may be provided, e.g., between flow meter 24a and heater 26, to provide additional feedback, e.g., if incoming fluid to heater 26 is colder than usual then power to the heater is increased. Although not illustrated, an airtrap may be provided to remove air from the fresh dialysis fluid prior to patient delivery. Heating the dialysis fluid tends to separate dissolved air from the dialysis fluid. It is accordingly contemplated to locate the airtrap downstream from heater 26, e.g., along line 18e upstream of temperature sensor 28.

Conductivity sensor 32, e.g., an inline conductivity sensor such as one or more graphite probe, is located between T or Y connector 30 and the patient so as to sense the conductivity of both fresh dialysis fluid (traveling to the patient in a first direction) and used dialysis fluid (traveling from the patient in a second direction). Conductivity sensor 32 is used to sense fresh dialysis fluid to make sure it is the proper type or blend, e.g., if different bagged dialysis fluids are provided for the patient, or if the fresh dialysis fluid is mixed online. Conductivity sensor 32 is used to sense used dialysis fluid to look for solute removal in the patient's effluent (e.g., for urea, $\beta_2$ microglobulin, and/or creatinine) or for signs of peritonitis. The flowpath of system 10a is configured such that a single conductivity sensor 32 is able to perform both fresh and used dialysis fluid functions. Conductivity sensor 32 is in one embodiment temperature compensated via the reading from temperature sensor 28. Additional conductivity sensors may be provided in the flowpath of system 10a as desired.

Pressure sensor 34, e.g., an inline pressure sensor, is located in the illustrated embodiment between conductivity sensor 32 and the patient. Pressure sensor 34 may alternatively be a pod pressure sensor or a transducer located within cycler 20a, where a pressure transmission tube extends from line 18h/18i to the transducer. The order of conductivity sensor 32 and pressure sensor 34 may be reversed although it may be advantageous to locate conductivity sensor 32 closer to temperature sensor 28. The output of pressure sensor 34 is used to ensure that (i) the positive pressure of fresh dialysis fluid delivered to the patient is within an allowable limit (e.g., 3.0 psig or less) and (ii) the negative pressure of used dialysis fluid removed from the patient is within an allowable limit (e.g., at or between −1.5 psig and zero psig). The flowpath of system 10a is likewise configured such that a single pressure sensor 34 is able to perform both fresh and used dialysis fluid functions. Additional pressure sensors may be provided in the flowpath of system 10a as desired.

Each of pumps 12a and 12b, valves 14a to 14d (and all valves described herein), and heater 26 are powered and controlled via a control unit 100, which includes one or more processor 102, one or more memory 104 and a video controller 106 for controlling a video monitor 108. Video monitor 108 is part of an overall user interface 110 for each of systems 10a to 10d described herein. User interface 110 includes any one or more of a touch screen overlay operable with video monitor 108 and/or one or more electromechanical input device, e.g., membrane switches, for inputting information into control unit. Video monitor 108 and speakers (e.g., operable with a sound card of control unit 100) are provided to output information to the patient or user, e.g., alarms, alerts and/or voice guidance commands.

Similarly, each of flow sensors 24a and 24b, temperature sensor 28, conductivity sensor 32 and pressure sensor 34 outputs to control unit 100. Control unit 100 uses the sensor outputs to control and monitor the components and their functions as described above for each of systems 10a to 10d described herein. Control unit 100 is programmed to run any of the flow sequences for systems 10a to 10d described below. Control unit 100 may also include a transceiver and a wired or wireless connection to a network, e.g., the internet, for sending treatment data to and receiving prescription instructions from a doctor's or clinician's server interfacing with a doctor's or clinician's computer.

Figure 2:
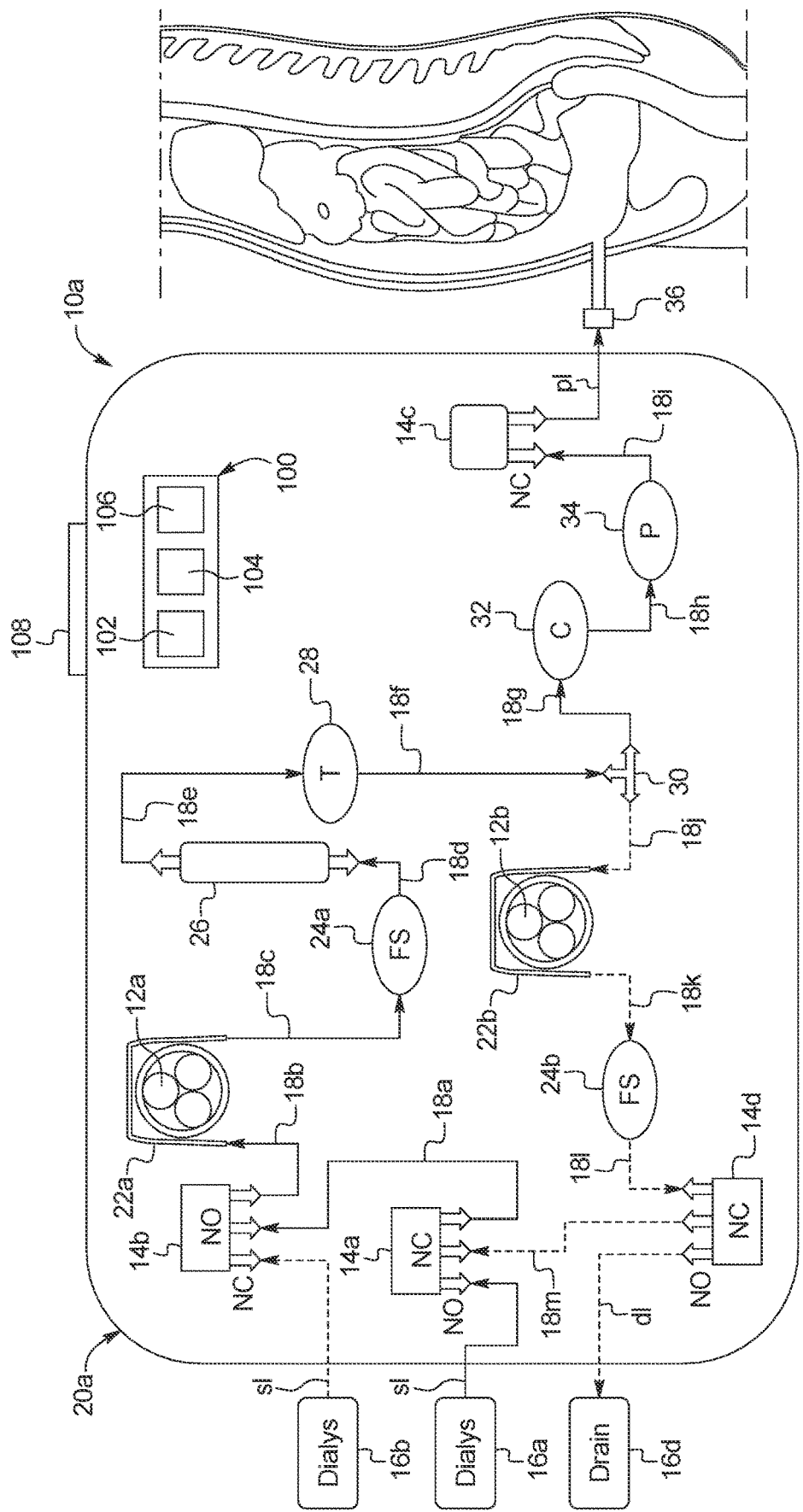
FIG. 2 is a flow schematic view of the first APD cycler embodiment during a patient fill phase.

Referring now to FIG. 2, system 10a is illustrated during one embodiment of a patient fill phase. In general, the solid lines indicate fresh dialysis fluid flow, while the dotted lines indicate no fluid flow. In the illustrated embodiment, control unit 100 causes fresh dialysis fluid pump 12a to pull fresh dialysis fluid from source 16a through valves 14a and 14b and to push the fresh dialysis fluid to heater 26. Flow sensor 24a located next to fresh dialysis fluid pump 12a detects fresh dialysis flow to heater 26 and outputs to control unit 100, which integrates flowrate over time to determine the amount of fresh dialysis fluid delivered to the patient and to ensure that the determined amount matches a prescribed amount. Heater 26 warms the dialysis fluid to a defined temperature, e.g., body temperature. Control unit 100 uses the output of temperature sensor 28 as feedback to ensure accurately warmed dialysis fluid is delivered to the patient. Conductivity sensor 32 measures the conductivity of fresh dialysis fluid and outputs to control unit 100, which checks to make sure the proper dialysis fluid is delivered to the patient. Pressure sensor 34 detects the positive pressure of the fresh dialysis fluid and outputs to control unit 100, which checks to make sure that the pressure is within a positive pressure limit, and modifies the speed of pump 12a as needed to stay within the limit. During the patient fill, normally closed patient valve 14c is energized to allow fresh dialysis fluid to fill the patient. When the fill is completed, patient valve 14c is deenergized so that it closes in a fail safe way. When all fluid in source 16a has been used, control unit 100 energizes valve 14b and possibly valve 14a to allow fluid to be pulled instead from dialysis fluid source 16b.

Figure 3:
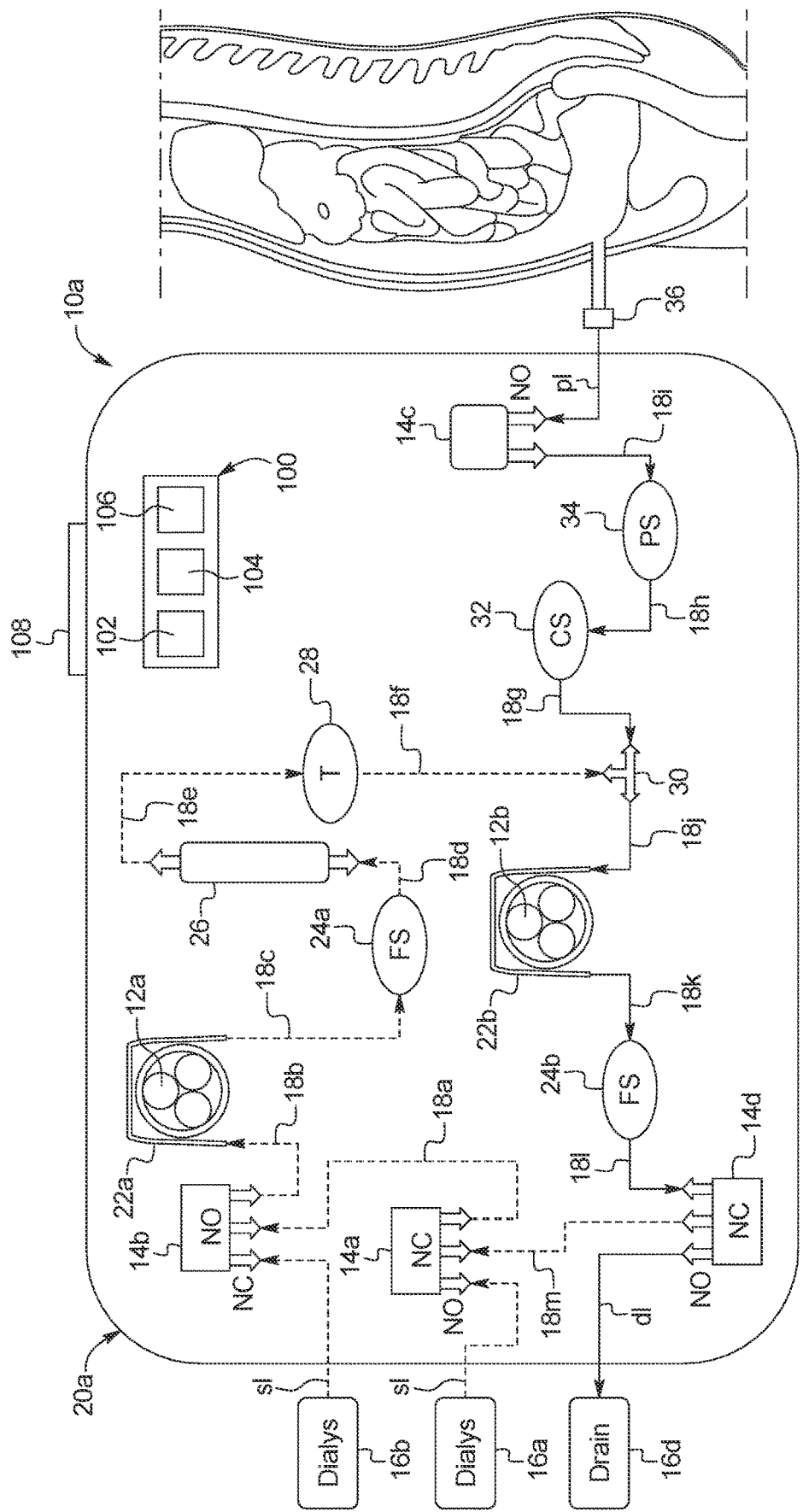
FIG. 3 is a flow schematic view of the first APD cycler embodiment during a patient drain phase.

Referring now to FIG. 3, system 10a is illustrated during one embodiment of a patient drain phase. Here, the solid lines indicate used dialysis fluid flow, while the dotted lines indicate no fluid flow. In the illustrated embodiment, control unit 100 energizes normally closed patient valve 14c and causes used dialysis fluid pump 12b to drain used dialysis fluid from the patient. Pressure sensor 34 detects the negative pressure of used dialysis fluid and outputs to control unit 100, which checks to make sure that the pressure is within a negative pressure limit, and modifies the speed of pump 12b as needed to stay within the limit. Conductivity sensor 32 measures the conductivity of the used dialysis fluid from the patient and outputs to control unit 100, which may determine and monitor any of the chemical and physiological levels or conditions discussed above, and/or send same over a network to a hospital or clinic to do the same. Used dialysis fluid flow sensor 24b located adjacent to used pump 12b detects used dialysis flow and outputs same to control unit 100, which integrates flowrate over time to determine the amount of used dialysis fluid removed from the patient and to ensure that at least a threshold prescribed amount of effluent is removed from the patient. In the illustrated embodiment, the NO port of drain valve 14d is connected to drain container 16d, such that drain valve 14d does not need to be energized for used dialysis fluid to flow to container 16d. In an alternative embodiment, drain container 16d is connected to the NC port of drain valve 14d.

Figure 4:
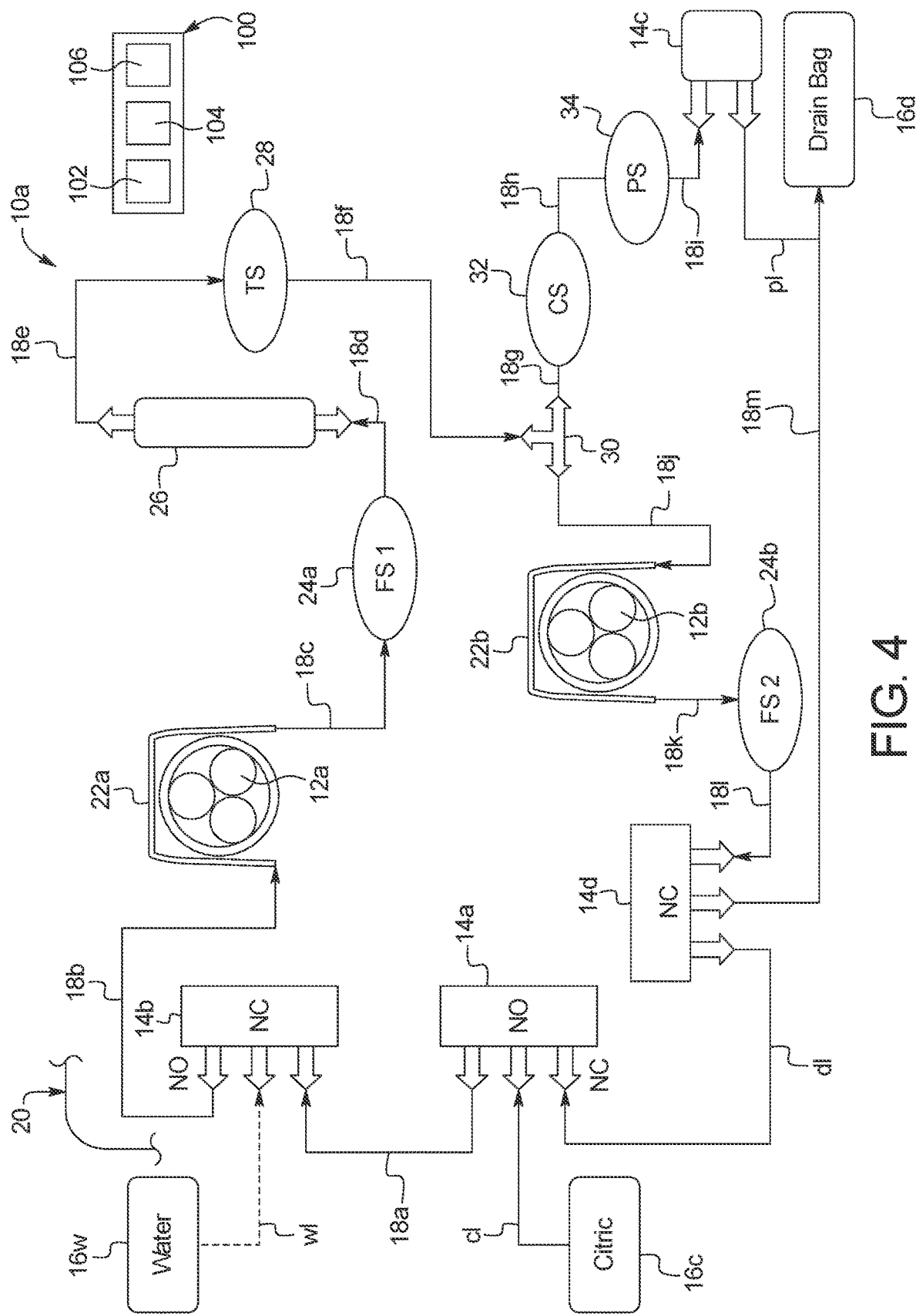
FIG. 4 is a flow schematic view of the first APD cycler embodiment during a chemical disinfectant portion of a disinfection sequence.
Figure 5:
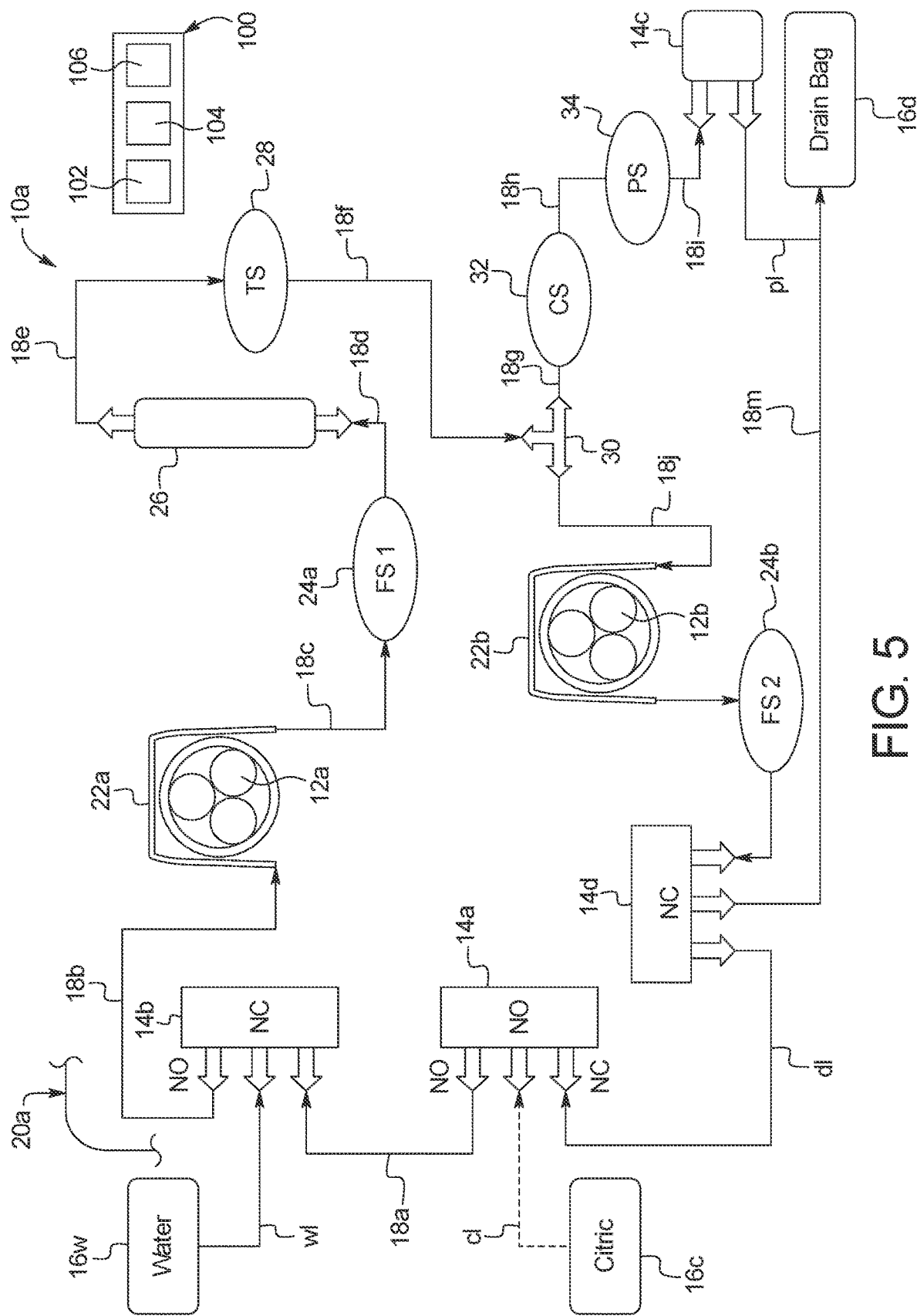
FIG. 5 is a flow schematic view of the first APD cycler embodiment during a purified water rinse portion of a disinfection sequence.

It should be appreciated that in many instances, the patient begins a new treatment already full of used dialysis fluid from the previous treatment or a midday exchange. In such a case for any of systems 10a to 10d, the sequence of FIG. 3 occurs before a first fill according to the sequence of FIG. 2. In either scenario, once each of the prescribed fills and drains has occurred, the present treatment as far as patient pumping is completed. In many known systems, the patient then removes a large amount of disposable items as part of a disposable set, which is then discarded. Systems 10a to 10d instead provide a disinfection sequence, which allows a large majority of the components described herein to be reused. FIGS. 4 and 5 illustrate that to configure system 10a for disinfection, the patient removes dialysis fluid sources 16a and 16b and associated solution lines and connects a disinfection source 16c, e.g., citric acid, to NO port of valve 14a via concentrate line cl, while a purified water source is connected to the NC port of valve 14b via a water line wl. One end of reused line 18m is removed from the NC port of valve 14a and is attached instead to drain container 16d along with the patient line pl. Drain line dl is removed from drain container 14d and is connected to the NC port of valve 14a.

FIG. 4 illustrates one embodiment of a disinfection flow sequence for system 10a in which concentrate line cl is solid to show flow, while water line wl is dotted to show no flow. Here, control unit 100 causes fresh pump 12a to pull disinfectant from source 16c and push same through heater 26, where it is heated to a disinfection temperature of, e.g., 90° C.±5° C. (or as defined for disinfection requirements), through each of the associated valves, lines 18a, 18b, 22a, 18c, 18d, 18e, 18f, 18h, 18i and patient line pl, connector 30 and sensors 24a, 28, 32 and 34 to drain container 16d. To do so, patient valve 14c is energized open. After a certain amount of heated disinfectant is delivered to drain container 16d, control unit 100 energizes valve 14a, stopping disinfectant from entering the flow circuit of system 10a, deenergizes (closes) patient valve 14c, and activates both pumps 12a and 12b to recirculate the disinfectant through the entire system for a predetermined amount of time via T or Y connector 30. Heater 26 may continue to heat the disinfectant to maintain the desired disinfection temperature. Control unit 100 may individually synchronize pumps 12a and 12b on and off as needed to maximize disinfection. Outputs from one or both of flow sensors 24a and 24b may be used to ensure that enough disinfection fluid resides within the closed fluid circuit. If needed, valve 14a may be deenergized (opened) to allow additional disinfection fluid to enter the closed circuit. The above cycles of (i) filling drain container 16d with heated disinfectant and (ii) recirculating the heated disinfectant throughout the closed circuit may be repeated a predetermined number of times, e.g., three to five times.

FIG. 5 illustrates one embodiment of a disinfection water rinse sequence for system 10a in which concentrate line cl is dotted to show no flow, while water line wl is solid to show flow. Here, control unit 100 energizes the NO port of valve 14b to allow pump 12a to pull purified water through water line wl. Patient valve 14c is also energized open to allow pump 12a to pump the purified water through sensors 24a, 28, 32 and 34 to drain container 16d and reusable line 18m. The above sequence is repeated until conductivity sensor 32 outputting to control unit 100 senses water instead of disinfectant. Control unit 100 then actuates pump 12b and deenergizes patient valve 14c, helping to allow water to flow through T or Y connector 30, flow sensor 24b and drain valve 14d into drain line dl. Valve 14a may be energized open to allow rinse water to flow to reusable line 18a, while valve 14d may be deenergized closed when the closed circuit is full of purified water to allow both pumps 12a and 12b to recirculate the water through the entire closed circuit. Control unit 100 may then repeat the above steps until only water conductivity is measured at conductivity sensor 32.

Figure 6:
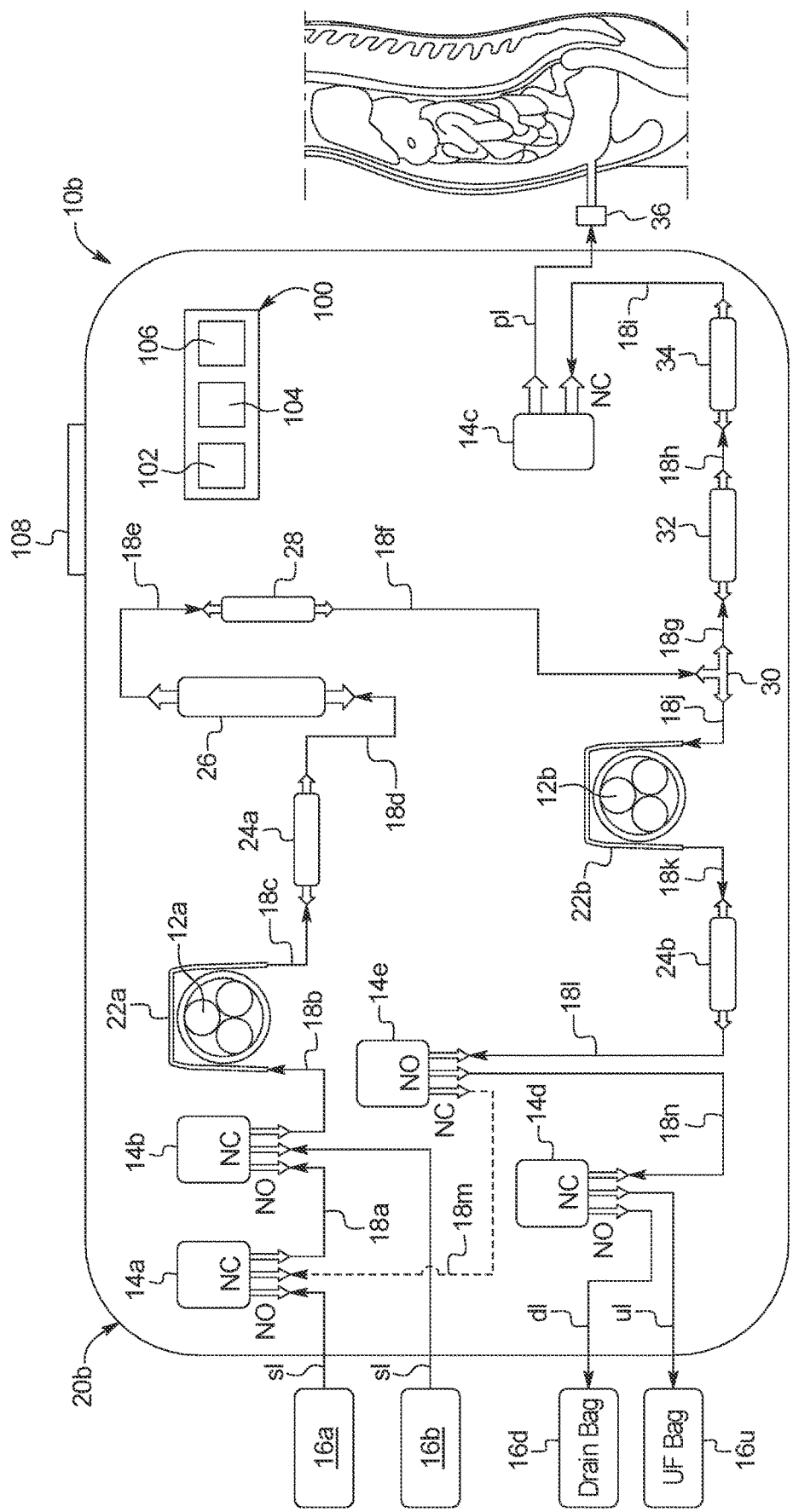
FIG. 6 is a flow schematic view of an alternative implementation of the first APD cycler embodiment, which includes a sample or ultrafiltration container.

FIG. 6 illustrates an alternative system 10b and cycler 20b of the present disclosure, which additionally includes a sample or ultrafiltration container or bag 16u and an additional three-way valve 14e, which is also under control of control unit 100. Each of the components in system 10b numbered the same as the components in system 10a includes all of the structure, functionality and alternatives discussed above for system 10a. In the illustrated embodiment, drain container or bag 16d is still placed in fluid communication with the NO port of drain valve 14d via drain line dl, while UF container or bag is placed in fluid communication with the NC port of drain valve 14d via UF or sample line ul. UF or sample line ul may be reusable or disposable. A fifth three-way valve 14e is located downstream from used dialysis fluid flow sensor 24b via reusable line 18l. The NC port of fifth valve 14e is placed in fluid communication with the NC port of first fresh dialysis fluid valve 14a via reusable line 18m, while the NO port of fifth valve 14e is placed in fluid communication with drain valve 14d. At certain desired times during treatment, e.g., once every drain phase, control unit 100 energizes drain valve 14d, causing effluent flow to drain bag or container 16d to stop and flow instead to UF container or bag 16u. The output from used dialysis fluid flow sensor 24b to control unit 100 enables the control unit to meter a desired amount of patient effluent into UF container or bag 16u. Afterwards, drain valve 14d is deenergized, allowing effluent flow to drain container or bag 16d to resume.

Figure 7:
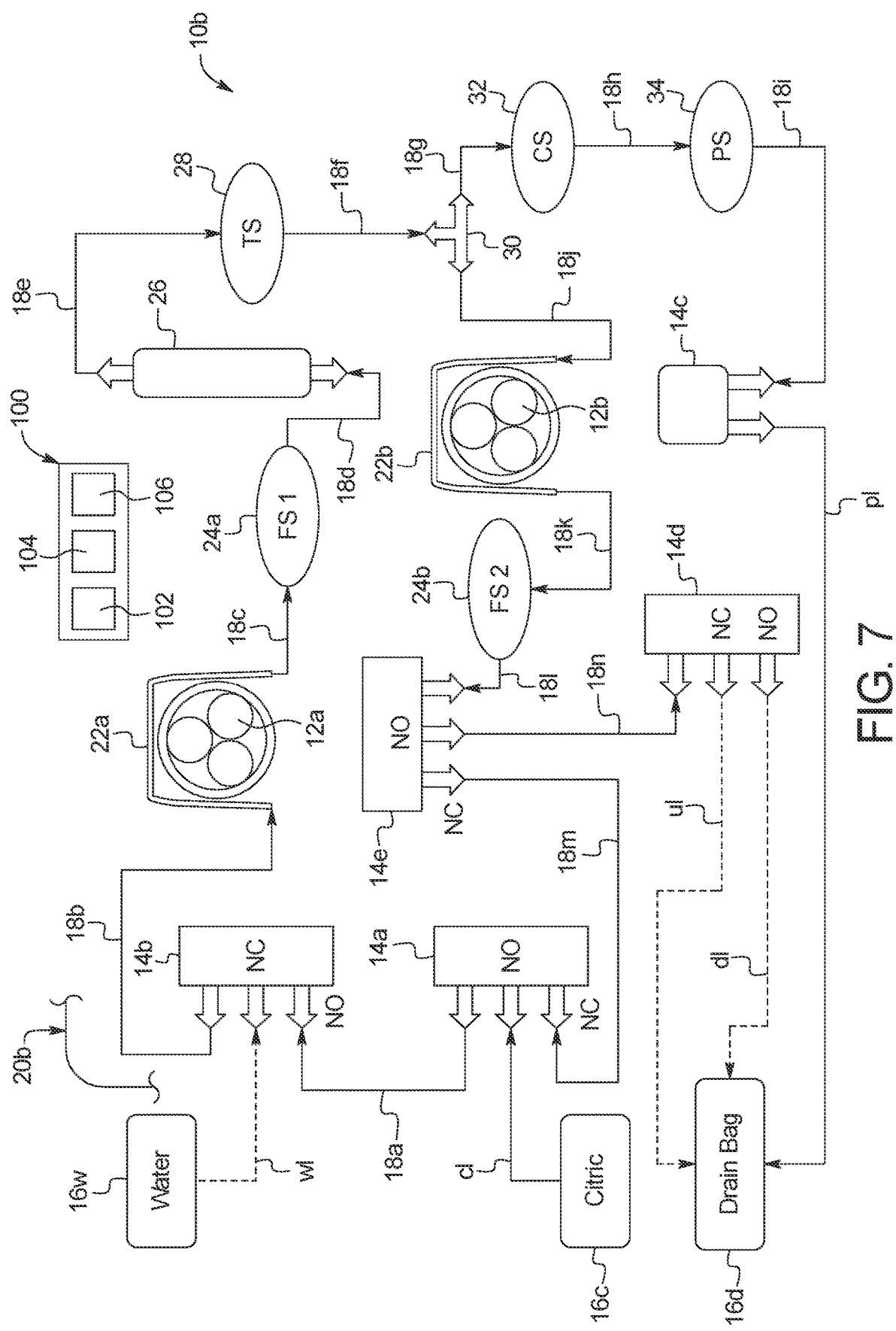
FIG. 7 is a flow schematic view of the alternative implementation of the first APD cycler embodiment during a chemical disinfectant portion of a disinfection sequence.
Figure 8:
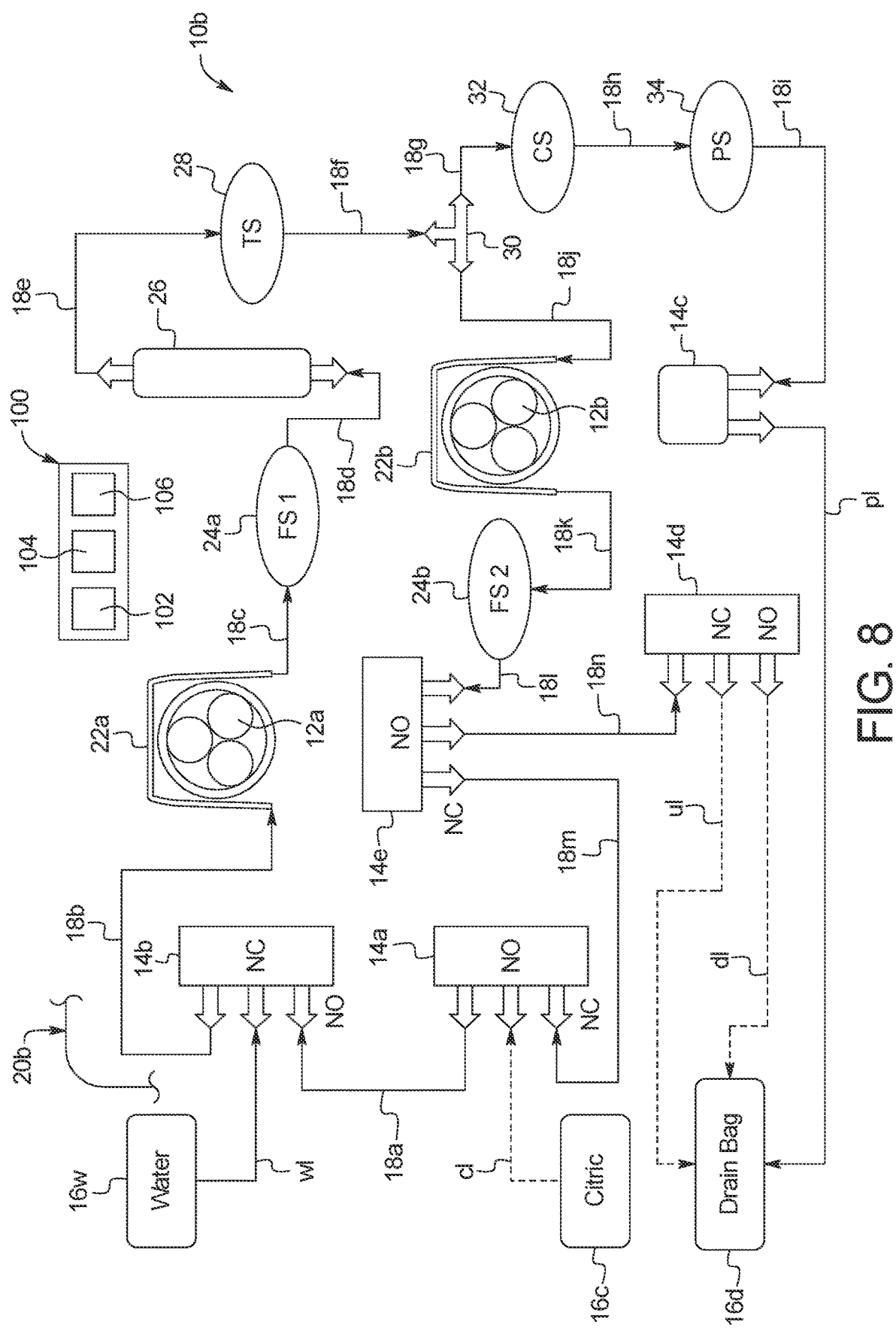
FIG. 8 is a flow schematic view of the alternative implementation of the first APD cycler embodiment during a purified water rinse portion of a disinfection sequence.

FIGS. 7 and 8 illustrate a chemical disinfectant portion and a purified water rinse portion of a disinfection sequence, respectively, for alternative system 10b. Here, first fresh dialysis fluid supply container 16a is replaced with disinfection source 16c, e.g., citric acid, which is placed in fluid communication with the NO port of first fresh dialysis fluid valve 14a via concentrate line cl. Second fresh dialysis fluid supply container 16b is replaced with purified water source 16w, which is placed in fluid communication with the NC port of second fresh dialysis fluid valve 14b via water line wl. UF container or bag 16u is removed and taken, for example, to a clinic for analysis. UF or sample line ul is connected instead to drain bag 16d. An additional reusable line 18n is added between drain valve 14d and the NO port of valve 14e. The patient disconnects patient line pl from transfer set 36 and connects it instead to drain bag 16d.

In FIG. 7 with concentrate line cl shown in solid for citric acid flow and purified water line wl shown dotted for no flow, control unit 100 actuates fresh dialysis fluid pump 12a to pull disinfectant from source 16c and push same through heater 26, where it is heated to a disinfection temperature of, e.g., 90° C.±5° C. (or as defined for disinfection requirements), through each of the associated valves, lines 18a, 18b, 22a, 18c, 18d, 18e, 18f, 18h, 18i and patient line pl, connector 30 and sensors 24a, 28, 32 and 34 to drain container 16d. To do so, patient valve 14c is energized open. After a certain amount of heated disinfectant is delivered to drain container 16d, control unit 100 energizes valve 14a, stopping disinfectant from entering the flow circuit of system 10a, deenergizes (closes) patient valve 14c, and activates both pumps 12a and 12b to recirculate the disinfectant through the entire system for a predetermined amount of time via T or Y connector 30. Heater 26 may continue to heat the disinfectant to maintain the desired disinfection temperature. Three-way valve 14e is maintained to allow disinfection fluid to reach drain valve 14d and drain line dl, and is at some point energized to allow the disinfection fluid to reach and disinfect reusable line 18n. Drain valve 14d is energized to allow disinfection fluid to disinfect UF or sample line ul. Simultaneously, control unit 100 may individually synchronize pumps 12a and 12b on and off as needed to maximize disinfection. Outputs from one or both of flow sensors 24a and 24b may be used to ensure that enough disinfection fluid resides within the closed fluid circuit. If needed, valve 14a may be deenergized (opened) to allow additional disinfection fluid to enter the closed circuit. The above cycles of (i) filling drain container 16d with heated disinfectant and (ii) recirculating the heated disinfectant throughout the closed circuit may be repeated a predetermined number of times, e.g., three to five times.

FIG. 8 illustrates one embodiment of a disinfection water rinse sequence for system 10b in which concentrate line cl is dotted to show no flow, while water line wl is solid to show flow. Here, control unit 100 energizes the NO port of valve 14b to allow pump 12a to pull purified water through water line wl. Patient valve 14c is also energized open to allow pump 12a to pump the purified water through sensors 24a, 28, 32 and 34 and patient line pl to drain container 16d and drain dl. The above sequence is repeated until conductivity sensor 32 outputting to control unit 100 senses water instead of disinfectant. Control unit 100 then actuates pump 12b and deenergizes patient valve 14c, helping to allow water to flow through T or Y connector 30, flow sensor 24b and added valve 14e into reusable line 18m. First fresh dialysis fluid valve 14a may be energized open to allow rinse water to flow to reusable line 18a, while drain valve 14d may be sequenced to allow purified water to selectively flow to drain bag 16d via drain line dl (valve 14d deenergized) or via UF or sample line ul (valve 14d energized) when the closed circuit is full of purified water to allow both pumps 12a and 12b to recirculate the water through the entire closed circuit. Control unit 100 may then repeat the above steps, e.g., three to five times, until only water conductivity is measured at conductivity sensor 32.

Figure 9:
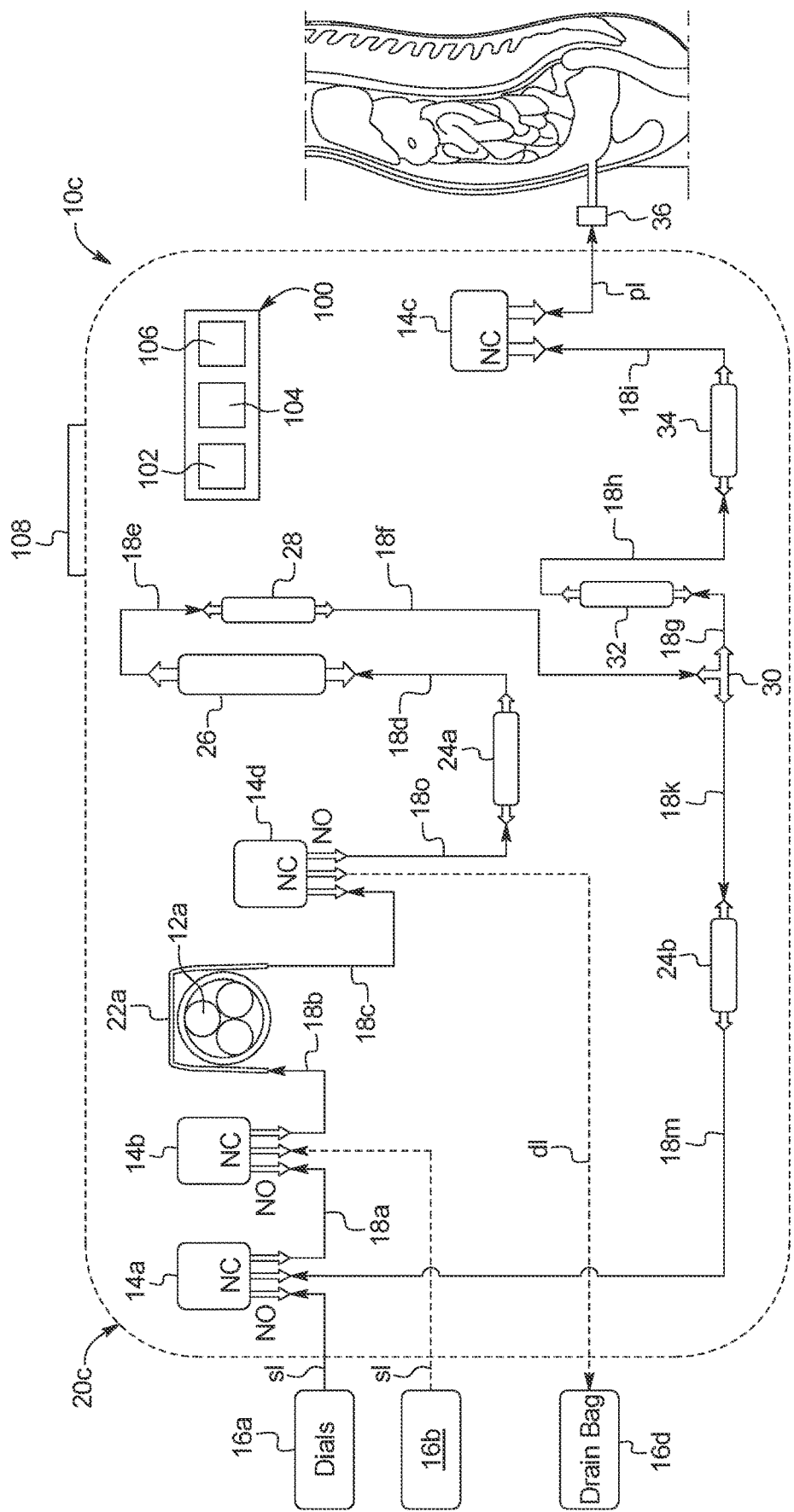
FIG. 9 is a flow schematic view of a second APD cycler embodiment of the present disclosure having a single pump, and which is configured for disinfection post treatment.

FIG. 9 illustrates an alternative system 10c and cycler 20c of the present disclosure, in which only single pump 12a (which may be any of the types of pumps discussed herein) under control of control unit 100 is provided. Each of the components in system 10c numbered the same as the components in systems 10a and 10b includes all of the structure, functionality and alternatives discussed above for systems 10a and 10b. In the illustrated embodiment, drain valve 14d is located between pump 12a and fresh dialysis fluid flow sensor 24a, wherein drain line dl extending from drain container or bag 16d is placed in fluid communication with NC port of drain valve 14e. Disinfectant and purified water are cycled through system 10c via T or Y connector 30 and reusable line 18m extending to NC port of fresh dialysis fluid valve 14a during disinfection.

Figure 10:
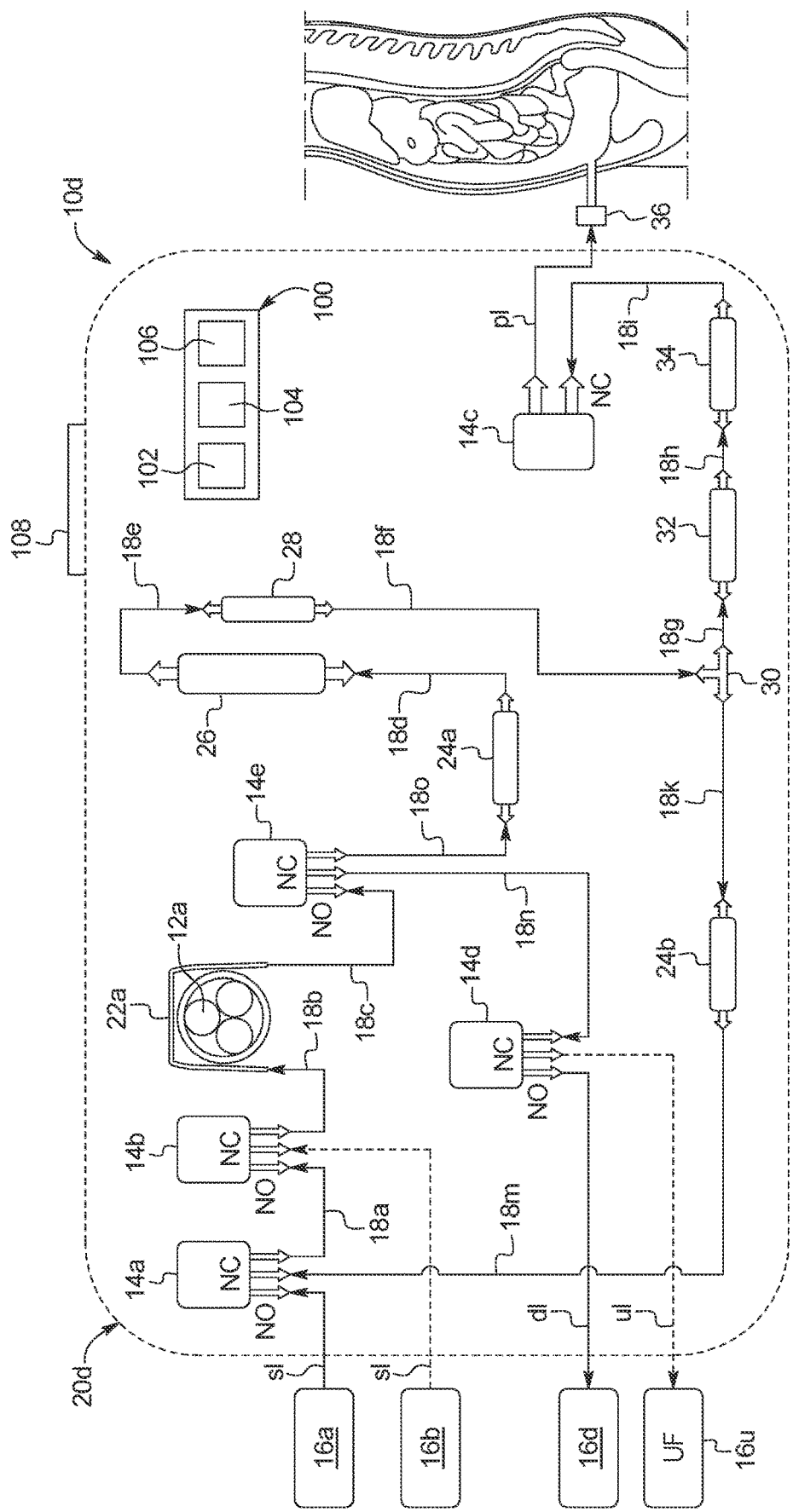
FIG. 10 is a flow schematic view of an alternative implementation of the second APD cycler embodiment, which includes a sample or ultrafiltration container.

FIG. 10 illustrates an alternative system 10d and cycler 20d of the present disclosure, in which only single pump 12a (which may be any of the types of pumps discussed herein) under control of control unit 100 is again provided. Each of the components in system 10d numbered the same as the components in systems 10a to 10c includes all of the structure, functionality and alternatives discussed above for systems 10a to 10c. In FIG. 10, sample or UF container 16u is added. In the illustrated embodiment, additional three-way valve 14e under control of control unit 100 is located between pump 12a and fresh dialysis fluid flow sensor 24a via additional line 18o, wherein another additional line 18n extends from NC port of valve 14e to drain valve 14d. As above, drain container 16d connects to NO of drain valve 14d via drain line dl, while sample or UF container 16u connects to NC of drain valve 14d via sample or UF line ul. Reusable line 18m extends again from T or Y connector 30 to NC port of fresh dialysis fluid valve 14a.

Figure 11:
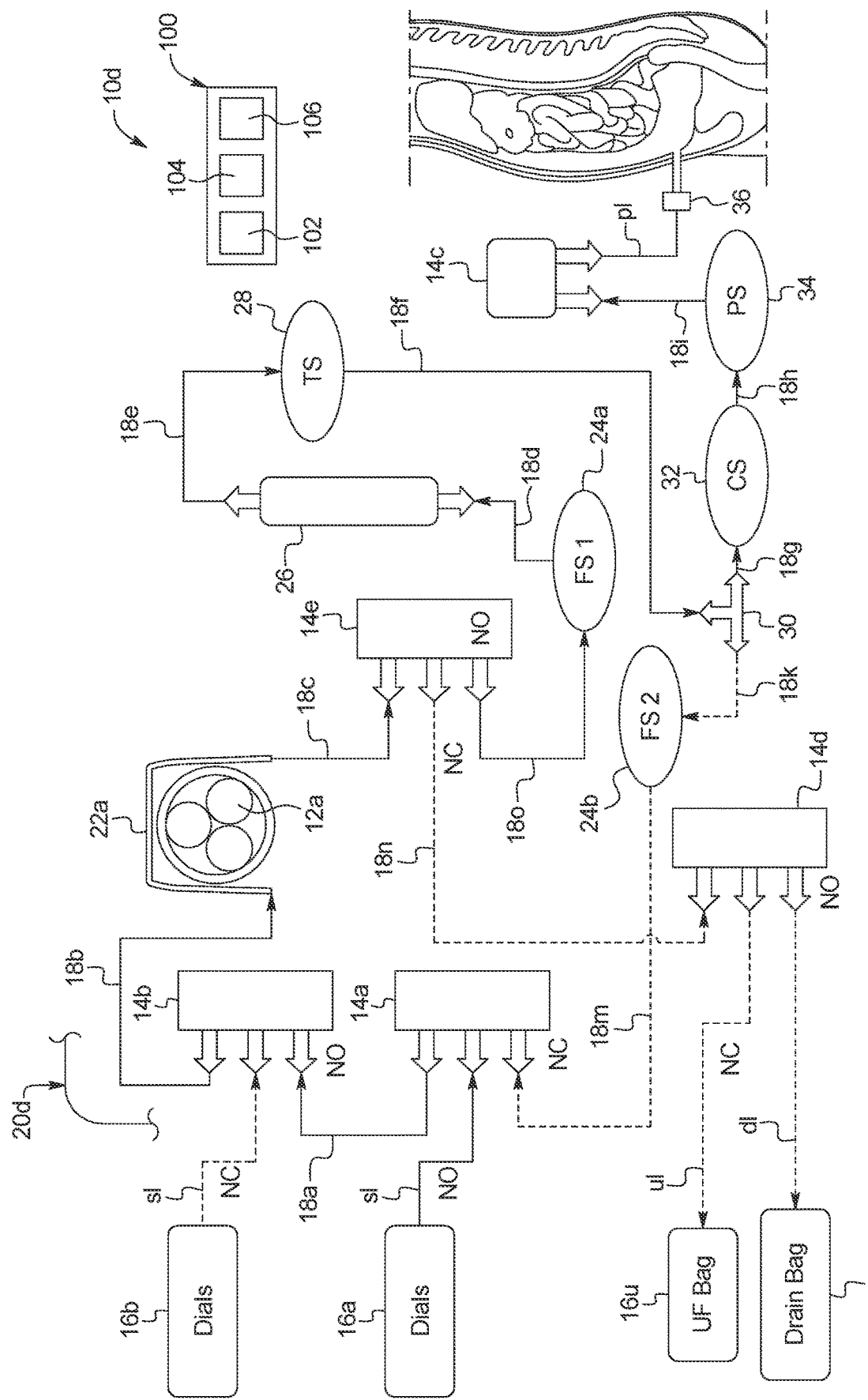
FIG. 11 is a flow schematic view of the alternative implementation of the second APD cycler embodiment during a patient fill phase.

Referring now to FIG. 11, system 10d is illustrated during one embodiment of a patient fill phase. In general, the solid lines indicate fresh dialysis fluid flow, while the dotted lines indicate no fluid flow. In the illustrated embodiment, control unit 100 causes fresh dialysis fluid pump 12a to pull fresh dialysis fluid from source 16a through valves 14a and 14b and to push the fresh dialysis fluid through heater 26 and the open path of valve 14e, to the patient. Flow sensor 24a located next to valve 14e detects fresh dialysis flow to heater 26 and outputs to control unit 100, which integrates flowrate over time to determine the amount of fresh dialysis fluid delivered to the patient and to ensure that the determined amount matches a prescribed amount. Heater 26 warms the dialysis fluid to a defined temperature, e.g., body temperature. Control unit 100 uses the output of temperature sensor 28 as feedback to ensure accurately warmed dialysis fluid is delivered to the patient. Conductivity sensor 32 located upstream from patient valve 14c measures the conductivity of fresh dialysis fluid and outputs to control unit 100, which checks to make sure the proper dialysis fluid is delivered to the patient. Pressure sensor 34 detects the positive pressure of the fresh dialysis fluid and outputs to control unit 100, which checks to make sure that the pressure is within a positive pressure limit, and modifies the speed of pump 12a as needed to stay within the limit. During the patient fill, normally closed patient valve 14c is energized to allow fresh dialysis fluid to fill the patient. When the fill is completed, patient valve 14c is deenergized so that it closes in a fail safe way. When all fluid in source 16a has been used, control unit 100 energizes valve 14b and possibly valve 14a to allow fluid to be pulled instead from dialysis fluid source 16b.

Figure 12:
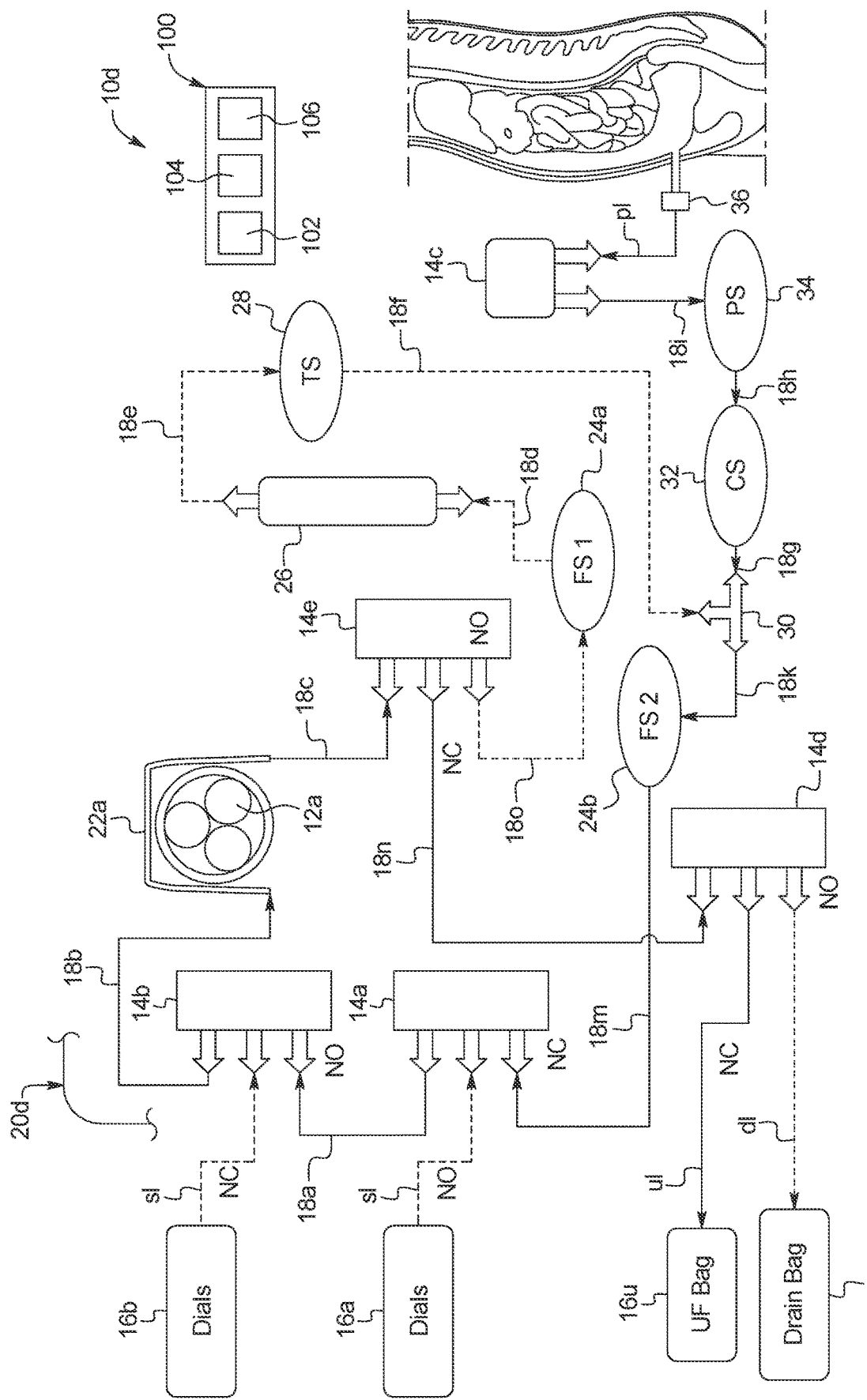
FIG. 12 is a flow schematic view of the alternative implementation of the second APD cycler embodiment during a patient drain phase.

Referring now to FIG. 12, system 10b is illustrated during one embodiment of a patient drain phase. Here, the solid lines indicate used dialysis fluid flow, while the dotted lines indicate no fluid flow. In the illustrated embodiment, control unit 100 energizes (i) normally closed patient valve 14c, (ii) valve 14a to close NO port to dialysis fluid flow and open NC port to receive effluent from the patient and (iii) valve 14e to close NO port of valve 14e to added line 18e and open NC port of valve 14e to allow effluent to flow through reusable line 18n to drain valve 14d, which is normally open to drain container 16d. Pressure sensor 34 detects the negative pressure of used dialysis fluid and outputs to control unit 100, which checks to make sure that the pressure is within a negative pressure limit, and modifies the speed of pump 12b as needed to stay within the limit. Conductivity sensor 32 measures the conductivity of the used dialysis fluid from the patient and outputs to control unit 100, which may determine and monitor any of the chemical and physiological levels or conditions discussed above, and/or send same over a network to a hospital or clinic to do the same. Used dialysis fluid flow sensor 24b located adjacent to T or Y connector 30 detects used dialysis flow and outputs same to control unit 100, which integrates flowrate over time to determine the amount of used dialysis fluid removed from the patient and to ensure that at least a threshold prescribed amount of effluent is removed from the patient. In the illustrated embodiment, the NO port of drain valve 14d is connected to drain container 16d, such that drain valve 14d does not need to be energized for used dialysis fluid to flow to container 16d.

As above, drain container 16d connects to NO of drain valve 14d via drain line dl, while sample or UF container 16u connects to NC of drain valve 14d via sample or UF line ul. At certain desired times during treatment, e.g., once every drain phase, control unit 100 energizes drain valve 14d, causing effluent flow to drain bag or container 16d to stop and flow instead to UF container or bag 16u. The output from used dialysis fluid flow sensor 24b to control unit 100 enables the control unit to meter a desired amount of patient effluent into UF container or bag 16u. Afterwards, drain valve 14d is deenergized, allowing effluent flow to drain container or bag 16d to resume.

Figure 13:
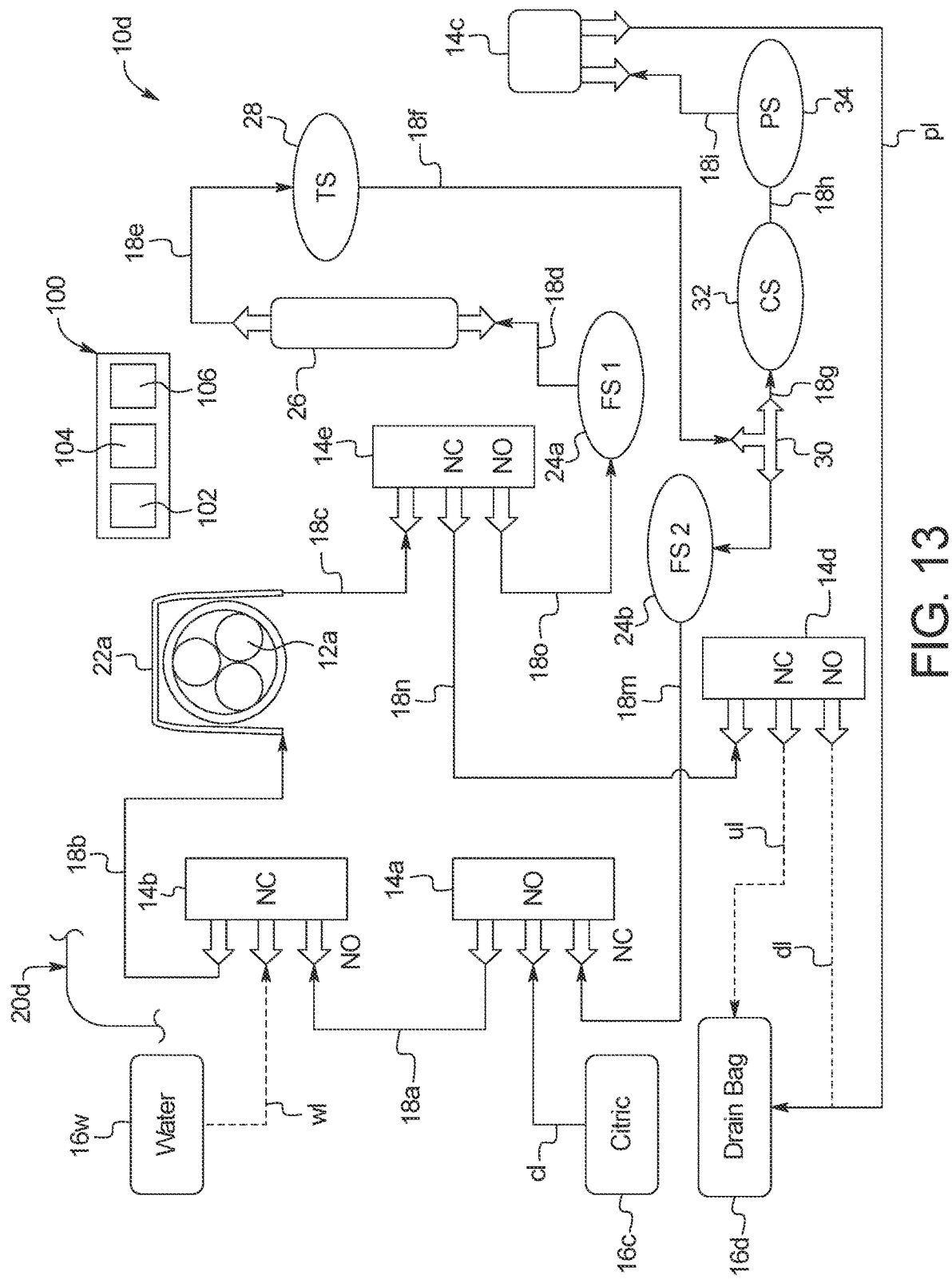
FIG. 13 is a flow schematic view of the alternative implementation of the second APD cycler embodiment during a chemical disinfectant portion of a disinfection sequence.
Figure 14:
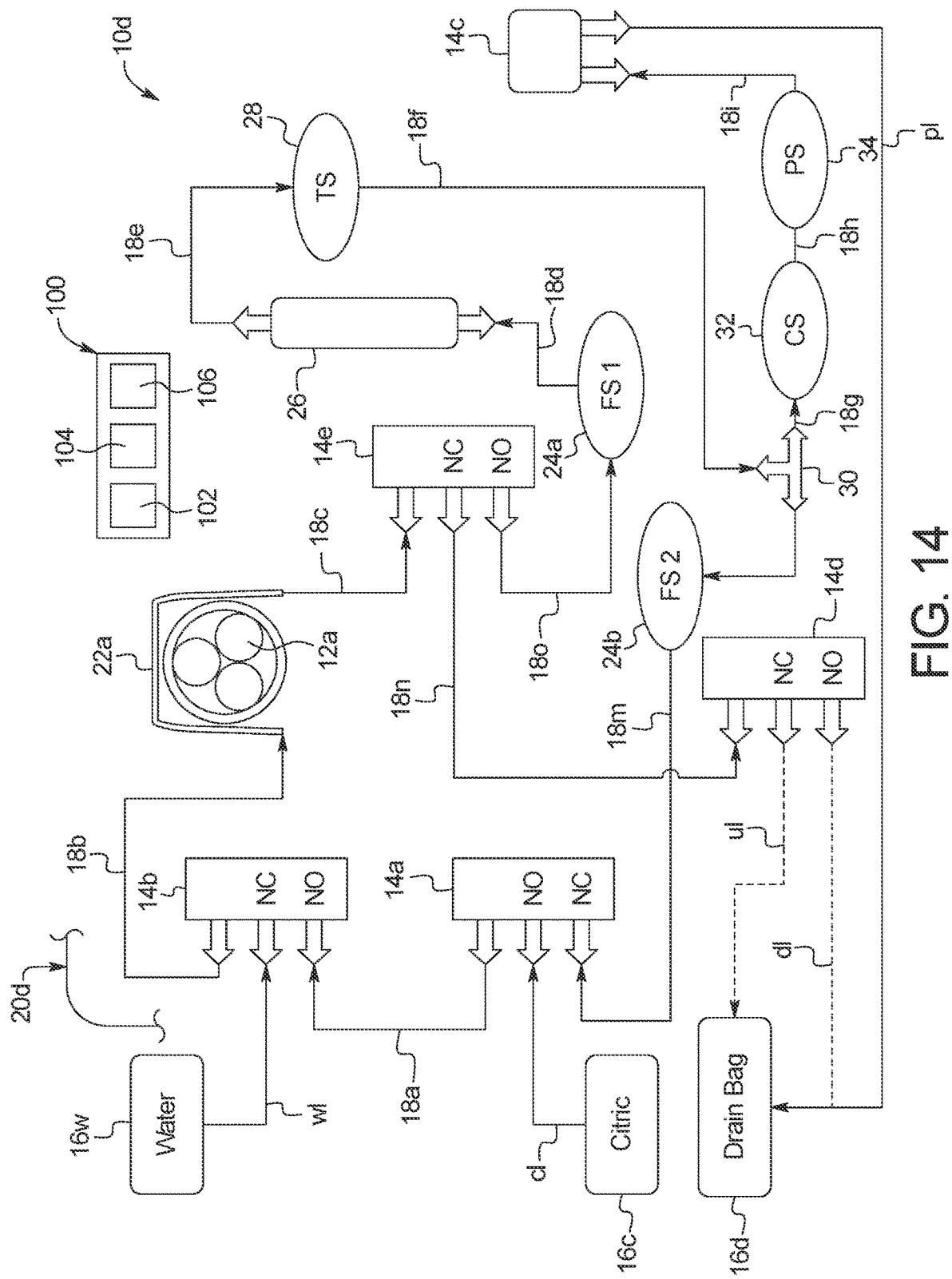
FIG. 14 is a flow schematic view of the alternative implementation of the second APD cycler embodiment during a purified water rinse portion of a disinfection sequence.

FIGS. 13 and 14 illustrate a chemical disinfectant portion and a purified water rinse portion of a disinfection sequence, respectively, for alternative system 10d. Here, first fresh dialysis fluid supply container 16a is replaced with disinfection source 16c, e.g., citric acid, is placed in fluid communication with the NO port of first fresh dialysis fluid valve 14a via concentrate line cl. Second fresh dialysis fluid supply container 16b is replaced with purified water source 16w, which is placed in fluid communication with the NC port of second fresh dialysis fluid valve 14b via water line wl. UF container or bag 16u is removed and taken, for example, to a clinic for analysis. UF or sample line ul is connected instead to drain bag 16d. Additional reusable line 18n is added between drain valve 14d and the NO port of valve 14e. The patient disconnects patient line pl from transfer set 36 and connects it instead to drain bag 16d.

In FIG. 13 with concentrate line cl shown in solid for citric acid flow and purified water line wl shown dotted for no flow, control unit 100 actuates fresh dialysis fluid pump 12a to pull disinfectant from source 16c and push same through heater 26, where it is heated to a disinfection temperature of, e.g., 90° C.±5° C. (or as defined for disinfection requirements), through each of the associated valves, lines 18a, 18b, 22a, 18c, 18o, 18d, 18e, 18f, 18h, 18i and patient line pl, connector 30 and sensors 24a, 28, 32 and 34 to drain container 16d. To do so, patient valve 14c is energized open. After a certain amount of heated disinfectant is delivered to drain container 16d, control unit 100 energizes valve 14a, stopping disinfectant from entering the flow circuit of system 10a, and activates both pumps 12a and 12b to recirculate the disinfectant through the entire system for a predetermined amount of time. Heater 26 may continue to heat the disinfectant to maintain the desired disinfection temperature. Three-way valve 14e is maintained to allow disinfection fluid to reach drain valve 14d and drain line dl, and is at some point energized to allow the disinfection fluid to reach and disinfect reusable line 18n. Drain valve 14d is energized to allow disinfection fluid to flow selectively to disinfect UF or sample line ul. Simultaneously, control unit 100 may individually synchronize pumps 12a and 12b on and off as needed to maximize disinfection. Outputs from one or both of flow sensors 24a and 24b may be used to ensure that enough disinfection fluid resides within the closed fluid circuit. If needed, valve 14a may be deenergized (opened) to allow additional disinfection fluid to enter the closed circuit. The above cycles of (i) filling drain container 16d with heated disinfectant and (ii) recirculating the heated disinfectant throughout the closed circuit may be repeated a predetermined number of times, e.g., 3 to 5 times.

FIG. 14 illustrates one embodiment of a disinfection water rinse sequence for system 10d in which concentrate line cl is dotted to show no flow, while water line wl is solid to show flow. Here, control unit 100 energizes the NO port of valve 14b to allow pump 12a to pull purified water through water line wl. Patient valve 14c is also energized open to allow pump 12a to pump the purified water through sensors 24a, 28, 32 and 34 and patient line pl to drain container 16d and drain dl. The above sequence is repeated until conductivity sensor 32 outputting to control unit 100 senses water instead of disinfectant. Control unit 100 then deenergizes patient valve 14c, helping to allow water to flow through T or Y connector 30, flow sensor 24b and added valve 14e into reusable line 18m. Fifth fluid valve 14e may be energized open to allow rinse water to flow through reusable line 18n to drain valve 14d, while drain valve 14d may be sequenced to allow purified water to selectively flow to drain bag 16d via drain line dl (valve 14d deenergized) or via UF or sample line ul (valve 14d energized) when the closed circuit is full of purified water to allow both pumps 12a and 12b to recirculate the water through the entire closed circuit. Control unit 100 may then repeat the above steps, e.g., three to five time, until only water conductivity is measured at conductivity sensor 32.

Figure 15:
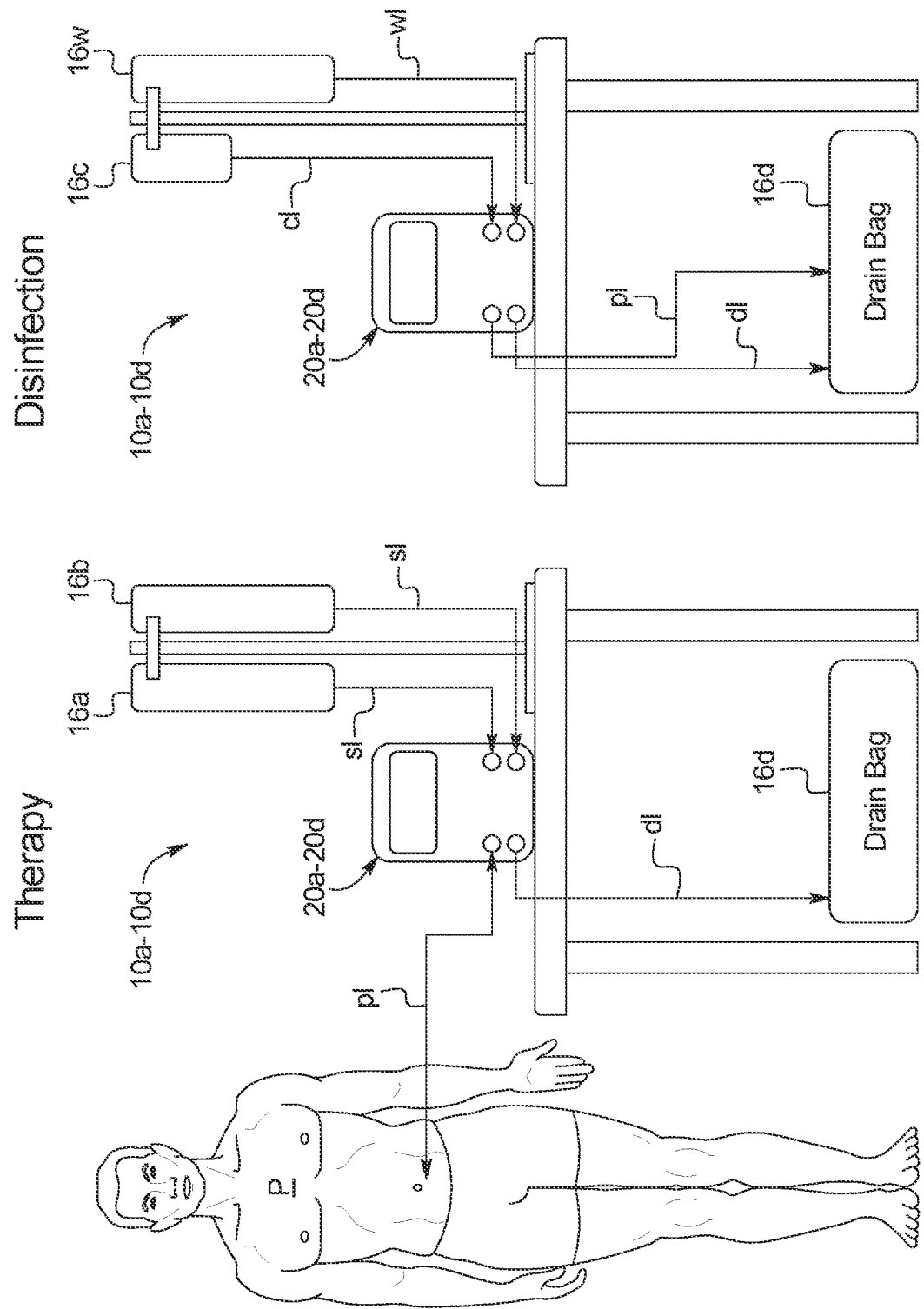
FIG. 15 is an elevation view of one embodiment of the APD cycler of the present disclosure having any flow schematic discussed herein illustrating both a treatment configuration and a disinfection configuration.

FIG. 15 illustrates an embodiment of systems 10a to 10d during therapy and disinfection. During therapy, fresh dialysis fluid supply containers 16a and 16b may be elevated as illustrated to enable gravity to aid fresh dialysis fluid flow. Containers 16a and 16b are oriented vertically to allow air to migrate to the top of the containers. Containers 16a and 16b are connected to cycler 20a to 20d via solution lines sl. Drain container 16d may be located beneath cycler 20a to 20d to aid drain fluid flow via gravity and is connected to cycler via drain line dl. The patient is connected to cycler 20a to 20d via patient line pl. As illustrated above, patient line pl, drain line dl and drain container 16d may be disinfected and reused, leaving only supply containers 16a and 16b and associated lines sl to be discarded after treatment. In an alternative embodiment supply lines sl are reused as concentrate and water lines cl and ul during disinfection.

During disinfection, concentrate container 16c and purified water container 16w replace fresh dialysis fluid supply containers 16a and 16b and are likewise elevated as illustrated to enable gravity to aid disinfection flow. Containers 16c and 16w are also oriented vertically to allow air to migrate to the top of the containers. Containers 16c and 16w are connected to cycler 20a to 20d via lines cl and wl, respectively. Drain container 16d is located again beneath cycler 20a to 20d to aid drain fluid flow via gravity and is connected to cycler via drain line dl. The patient is disconnected from cycler 20a to 20d. As illustrated above, patient line pl and drain line dl are connected to drain container 16d during disinfection and are thus reused. Where a UF or sample bag 16u is provided, UF line ul extending from cycler 20a to 20d is likewise connected to drain container 16d.

It should be understood that various changes and modifications to the presently preferred embodiments described herein will be apparent to those skilled in the art. For example, while the fluid schematics illustrated herein show connections to specific NO and NC ports of valves 14a to 14e forming one workable overall flow schematic, the present disclosure is not limited to the specific NO and NC connections, and those of skill may determine others. Also, while a combined chemical and heat disinfection is disclosed, chemical or heat alone may be sufficient. Other types of disinfection, e.g., ultraviolet light, may be used additionally or alternatively. It is therefore intended that such changes and modifications be covered by the appended claims.

The invention is claimed as follows:

1. A peritoneal dialysis ("PD") system comprising:
   a dialysis fluid pump including a pump actuator and a dialysis fluid contacting portion actuated by the pump actuator;
   a fresh dialysis fluid valve located upstream of the dialysis fluid pump, the fresh dialysis fluid valve including a fresh valve actuator and a dialysis fluid contacting portion actuated by the fresh valve actuator;
   a patient line valve located downstream from the dialysis fluid pump, the patient line valve including a patient line valve actuator and a dialysis fluid contacting portion actuated by the patient line valve actuator;
   a drain valve positioned and arranged to receive used dialysis fluid from a patient, the drain valve including a drain valve actuator and a dialysis fluid contacting portion;
   first and second dialysis fluid sources;
   a disinfection source;
   a purified water source; and
   a control unit configured to
   (i) cause the pump actuator to actuate, and the fresh valve actuator, the patient line valve actuator and the drain valve actuator to actuate or not actuate their respective dialysis fluid contacting portions according to a programmed fill sequence to perform a PD fill phase using the first or second dialysis fluid sources,
   (ii) cause the pump actuator to actuate, and the fresh valve actuator, the patient line valve actuator and the drain valve actuator to actuate or not actuate their respective dialysis fluid contacting portions according to a programmed drain sequence to perform a PD drain phase, and
   (iii) after actions (i) and (ii), or after actions (i) and (ii) are repeated at least one time, and with the first and second dialysis fluid sources replaced by the disinfection source and the purified water source, cause the pump actuator to actuate, and the fresh valve actuator, the patient line valve actuator and the drain valve actuator to actuate or not actuate their respective dialysis fluid contacting portions according to a programmed disinfection sequence to disinfect the respective dialysis fluid contacting portions of each of the pump actuator, the fresh valve actuator, the patient line valve actuator and the drain valve actuator using disinfectant from the disinfection source, after which the purified water source is used to rinse the disinfectant.

2. The PD system of claim 1, wherein the disinfection sequence is further configured to disinfect at least one of (a) a first fluid line leading from one of the dialysis fluid sources to the dialysis fluid contacting portion of the fresh dialysis fluid valve, (b) a second fluid line leading from the dialysis fluid contacting portion of the fresh dialysis fluid valve to the dialysis fluid contacting portion of the dialysis fluid pump, (c) a third fluid line leading from the dialysis fluid contacting portion of the dialysis fluid pump, (d) a fourth fluid line leading to the dialysis fluid contacting portion of the patient line valve, (e) a fifth fluid line leading from the dialysis fluid contacting portion of the patient line valve, (f) a sixth fluid line leading to the dialysis fluid contacting portion of the drain valve, or (g) a seventh fluid line leading from the dialysis fluid contacting portion of the drain valve.

3. The PD system of claim 2, wherein at least one of the first fluid line, the second fluid line, the third fluid line, the fourth fluid line, the fifth fluid line, the sixth fluid line or the seventh fluid line is made of metal or a biocompatible and heat-disinfectable flexible tube.

4. The PD system of claim 1, wherein the dialysis fluid contacting portion of at least one of the fresh dialysis fluid valve, the patient line valve or the drain valve includes a tube or membrane.

5. The PD system of claim 1, wherein the dialysis fluid contacting portion of at least one of the fresh dialysis fluid valve, the patient line valve or the drain valve includes an internal cavity of the respective one of the fresh valve actuator, the patient line valve actuator, or the drain valve actuator.

6. The PD system of claim 1, wherein the dialysis fluid contacting portion of the dialysis fluid pump includes a tube or membrane.

7. The PD system of claim 1, wherein the dialysis fluid contacting portion of the dialysis fluid pump includes an internal cavity of the pump actuator.

8. The PD system of claim 1, wherein the dialysis fluid contacting portion of the patient line valve is placed in fluid communication with the dialysis fluid contacting portion of the drain valve for operation of the programmed disinfection sequence.

9. The PD system of claim 1, wherein the dialysis fluid contacting portion of the patient line valve is placed in fluid communication with a drain container connected fluidly with the dialysis fluid contacting portion of the drain valve for operation of the programmed disinfection sequence.

10. The PD system of claim 1, wherein the disinfectant includes citric acid.

11. The PD system of claim 1, wherein the fresh dialysis fluid valve is a first fresh dialysis fluid valve, the fresh valve actuator is a first fresh valve actuator, and the dialysis fluid contacting portion actuated by the fresh valve actuator is a first dialysis fluid contacting portion actuated by the first fresh valve actuator, and wherein the PD system further includes a second fresh dialysis fluid valve located upstream of the dialysis fluid pump, the second fresh dialysis fluid valve including a second fresh valve actuator and a second dialysis fluid contacting portion actuated by the second fresh valve actuator, wherein the first and second dialysis fluid sources are placed in fluid communication with the first and second dialysis fluid contacting portions of the respective first and second fresh dialysis fluid valves for the PD fill phase in action (i).

12. The PD system of claim 1, wherein the control unit is configured to use the dialysis fluid pump to pump fresh dialysis fluid during the PD fill phase in action (i) and to pump used dialysis fluid during the PD drain phase in action (ii).

13. The PD system of claim 1, wherein the dialysis fluid pump is a fresh dialysis fluid pump and the pump actuator is a fresh dialysis fluid pump actuator for pumping fresh dialysis fluid during the PD fill phase in action (i), and wherein the PD system further includes a used dialysis fluid pump including a used dialysis fluid pump actuator for pumping used dialysis fluid during the PD drain phase in action (ii), and wherein the control unit is configured to cause the fresh dialysis fluid pump actuator, the used dialysis fluid pump actuator, the fresh valve actuator, the patient line valve actuator and the drain valve actuator to actuate or not actuate their respective dialysis fluid contacting portions according to the programmed disinfection sequence.

14. The PD system of claim 13, wherein the fresh dialysis fluid pump actuator and the used dialysis fluid pump actuator are actuated during the programmed disinfection sequence, and wherein at least a portion of each of the fresh valve actuator, the patient line valve actuator and the drain valve actuator is fluidically open during the programmed disinfection sequence.

15. The PD system of claim 1, wherein the pump actuator is actuated during the programmed disinfection sequence, and wherein at least a portion of each of the fresh valve actuator, the patient line valve actuator and the drain valve actuator is fluidically open during the programmed disinfection sequence.

* * * * *